(12) United States Patent
Klass et al.

(10) Patent No.: US 6,993,402 B2
(45) Date of Patent: Jan. 31, 2006

(54) METHOD AND SYSTEM FOR IDENTIFYING AND ANTICIPATING ADVERSE DRUG EVENTS

(75) Inventors: David B. Klass, Westchester, IL (US); Adam P. Klass, Oak Park, IL (US); Dennis Joseph Ring, Shakopee, MN (US)

(73) Assignee: VigiLanz Corporation, St. Paul, MN (US)

( * ) Notice: Subject to any disclaimer, the term of this patent is extended or adjusted under 35 U.S.C. 154(b) by 450 days.

(21) Appl. No.: 09/970,320

(22) Filed: Oct. 3, 2001

(65) Prior Publication Data

US 2002/0120350 A1     Aug. 29, 2002

Related U.S. Application Data

(60) Provisional application No. 60/272,019, filed on Feb. 28, 2001.

(51) Int. Cl.
*G06F 19/00* (2006.01)

(52) U.S. Cl. .................... 700/103; 700/90; 705/3; 702/188

(58) Field of Classification Search .............. 700/90, 700/103, 108; 705/1–3; 702/188
See application file for complete search history.

(56) References Cited

U.S. PATENT DOCUMENTS

| | | | |
|---|---|---|---|
| 5,827,180 A * | 10/1998 | Goodman | 600/300 |
| 6,000,828 A * | 12/1999 | Leet | 705/2 |
| 6,356,873 B1 * | 3/2002 | Teagarden et al. | 705/3 |
| 6,731,989 B2 * | 5/2004 | Engleson et al. | 700/19 |
| 2002/0040282 A1 * | 4/2002 | Bailey et al. | 702/188 |
| 2002/0095313 A1 * | 7/2002 | Haq | 705/2 |
| 2003/0028811 A1 * | 2/2003 | Walker et al. | 713/202 |

OTHER PUBLICATIONS

"Computerized Monitoring of Valproate and Physician Responsiveness to Laboratory Studies as a Quality Indicator", Daniel J. Luchins, M.D., et al,; Psychiatric Services, Sep. 2000, vol. 51, No. 9.

* cited by examiner

*Primary Examiner*—Jayprakash N. Gandhi
(74) *Attorney, Agent, or Firm*—Dorsey & Whitney LLP

(57) ABSTRACT

The present invention is a system and method for anticipating potential Adverse Drug Events (ADE) in a patient's medication regimen by integrating data typically located in laboratory and pharmacy information systems and filtering the data using predefined criteria. The present invention includes a system for anticipating a possible ADE through the use of a search engine that compares integrated data from laboratory and pharmacy information systems and compares it to predefined ADE rules defining normal ranges for a particular laboratory test. If an abnormal test value is received and a drug in the patient's medication regimen satisfies a drug included in an ADE rule then an alert procedure is triggered which allows for a period of time wherein the patient's lab and pharmacy data is monitored in order to determine if a proper corrective action is undertaken, and if no corrective action or an improper corrective action is taken within that period of time, the healthcare provider is warned of a potential ADE.

33 Claims, 26 Drawing Sheets

Fig. 7

| | Parameter | Description |
|---|---|---|
| 71 | Search Status | Status of Drug/Lab Search: Enabled/Disabled. Search is performed only if it is "Enabled" |
| 72 | Search Type | Type of Drug/Lab Search: Alert or Research. "Alert" type WILL generate alerts; "Research" type will Not generate an alert. |
| 73 | Target Drug | Name of "Target" Drug. Note: All drug names are automatically extracted from the pharmacy import data file. |
| 74 | Target Lab | Name of the lab test. Note: All lab names are automatically extracted from the lab import data file. |
| 75 | Drug/Lab Search Name | Unique identifier of this drug/lab pair search |
| 76 | Severity | Severity of the ADE. |
| 77 | Lab Code | Abbreviation or acronym for the lab test. |
| 78 | Pattern | Pattern specifies two things: First, if this Drug/Lab Search looking for a "high" lab test or a "low" lab test? Second, what is the "normal" drug response to lab test (i.e. To "raise" the drug dosage, or to "lower" the drug dosage. |
| 79 | Type | High or low type of lab test. "High" -Drug/Lab Search set to look for a "high" lab test result; "Low" -lab test set to look for a "low" lab test result. |
| 80 | Baseline | The lab test value at which point the lab test is considered "abnormal". |
| 81 | Absolute | The lab test value at which point the lab test is considered a "medical emergency". |
| 82 | Interval | The amount of time that would typically be allowed to respond, based upon an abnormal lab test. |
| 83 | Danger Multiplier | A value is entered which shortens the "Interval" as the lab test result value gets closer to the "Absolute" level. |
| 84 | Momentum Multiplier | A value is entered which shortens or lengthens the "interval" based upon the previous lab test result value. |
| 85 | Allergy | Allergy test indicator. |
| 86 | Hospital Unit(s) | A set of "Hospital Units" to which this Drug/Lab Search applies. |
| 87 | Doctor(s) | A set of "Doctor(s)" to which this Drug/Lab Search applies. |
| 88 | Diagnosis(s) | A set of "Diagnoses" to which this Drug/Lab Search applies. |
| 89 | Gender | Identifies whether one, or both sexes are applied to this Drug/Lab Search. |
| 90 | Age Range | Identifies if the age range to which this Drug/Lab Search applies. |
| 91 | Concurrent Drug | Name of "Drug(s)" that must currently be prescribed to the patient. Up to three other Drugs may be specified. |
| 92 | Concurrent Lab | Name of "Lab(s)" that must currently be prescribed to the patient. Up to three other Labs may be specified. |
| 93 | Alert Template | Name of the template that defines how to handle an "alert" for this Drug/Lab Search. |
| 94 | Description | A user provided description of the ADE Search. |
| 95 | Contact | Who should be contacted for questions regarding this ADE Search? |

| ADE Individual Results | | Last Run 03/01/2000 to 03/31/2000 11:59:00 P.M. | |
|---|---|---|---|

Name of Search: ▽
○ Facility: ▽
○ Pass or Fail ▽
○ Result ▽

○ Doctor: ▽
○ Patient ID: ▽
○ All

— Results —

| Search Name | Lab Test | Drug | Pass or Fail | Facility |
|---|---|---|---|---|
| AMMONIA_DIVALPROEX | AMMONIA BLOOD | DIVALPROEX | Fail | Facility |
| AMMONIA_DIVALPROEX | AMMONIA BLOOD | DIVALPROEX | Fail | Facility |
| AMMONIA_DIVALPROEX | AMMONIA BLOOD | DIVALPROEX | Wait | Facility |
| AMMONIA_DIVALPROEX | AMMONIA BLOOD | DIVALPROEX | Fail | Facility |
| AMMONIA_DIVALPROEX | AMMONIA BLOOD | DIVALPROEX | Fail | Facility |
| carbamazepine_CARBAMAZEPINE_H/L_High | CARBAMAZEPINE | CARBAMAZEPINE | Pass | Facility |
| carbamazepine_CARBAMAZEPINE_H/L_High | CARBAMAZEPINE | CARBAMAZEPINE | Fail | Facility |
| carbamazepine_CARBAMAZEPINE_H/L_High | CARBAMAZEPINE | CARBAMAZEPINE | Fail | Facility |
| carbamazepine_CARBAMAZEPINE_H/L_High | CARBAMAZEPINE | CARBAMAZEPINE | Pass | Facility |
| carbamazepine_CARBAMAZEPINE_H/L_High | CARBAMAZEPINE | CARBAMAZEPINE | Fail | Facility |
| carbamazepine_CARBAMAZEPINE_H/L_High | CARBAMAZEPINE | CARBAMAZEPINE | Fail | Facility |
| carbamazepine_CARBAMAZEPINE_H/L_High | CARBAMAZEPINE | CARBAMAZEPINE | Fail | Facility |

[Show Graph] [Print All]

[Print]    06/11/2001 9:45am

Hospital Logo
(Home Page)

Alert Summary Listing

Scope of Alerts
- Hospital
- Unit [CCU ▽]
- Doctor [Adams, John ▽]

Category of Alerts
- By Severity [Severe ▽]
- By Type [Time Expired ▽]

Alert Timeframe
- 1 week
- 1 month
- 3 months
- 6 months
- 12 months
- 24 months View Summary of Alerts

| Alert Rule Name | #Occurrences | #Alerts | %Alerts |
|---|---|---|---|
| Dilantin PHENYTOIN H/L High | | | |
| | | | |
| | | | |
| | | | |
| | | | |
| | | | |

⟷

Alert View
Alert Analysis
Rule View
Rule Maintenance
User Maintenance
Alert Templates
Hospital Maintenance
Operations

Fig 17b

Hospital Logo
(Home Page)

Rule Maintenance (Add/ Update)                                    ☒

Rule Name: Dilantin_PHENYTOIN_H/L_High

Drug:      PHENYTOIN   ▽         Severity
Lab:       DILANTIN    ▽          o Severe
Contact:   Adams, Joe  ▽          o Intermediate
Status:    o Enabled  o Disabled  o Basic
Dates:     04/13/2001  ▽
           07/11/2001.            Age
Unit:      ICU         ▽          From:  05  ▽
Doctor:    Smith, Harry ▽         To:    12  ▽
Diagnosis:             ▽
                                  Gender
                                   o Both
                                   o Female
                                   o Male Lab Values Pattern:   H/L   ▽    Baseline:  1.0  ▽
Type:      H/L   ▽    Absolute:  1.0  ▽

⇨

Alert View
Alert Analysis
Rule View
Rule Maintenance
User Maintenance
Alert Templates
Hospital Maintenance
Operations

Fig 19a

METHOD AND SYSTEM FOR IDENTIFYING AND ANTICIPATING ADVERSE DRUG EVENTS

CROSS-REFERENCE TO RELATED APPLICATION(S)

This application claims priority from U.S. provisional application No. 60/272,019, filed Feb. 28, 2001 the contents of which are incorporated herein in its entirety.

TECHNICAL FIELD

This invention relates to a method and system for managing and anticipating adverse drug events ("ADE"). More particularly, the invention relates to a method and system for integrating and using data from a medical facility's pharmacy and laboratory information systems to anticipate potential ADEs in a patient's medication regiment.

BACKGROUND OF THE INVENTION

A number of preventable patient care errors occur because the prescription of medication to a patient is done without first consulting a patient's laboratory results. Some patients have had drugs continuously administered to them for hours or days after toxic levels for that drug are recorded by the lab. Some patients have received particular medication long after the laboratory has documented signs of drug-related side effects. Others have received erroneous laboratory test results because their medication interferes with the laboratory tests they are undergoing. Still others have received medications even after the patient's lab result indicates that it is dangerous to do so. All these errors, and many more not mentioned, could have all been prevented if a patients laboratory results were consulted prior to prescribing or administrating a medication.

These errors occur for many reasons. At times, a physician is ordering certain medications at a site remote from a medical facility and so is not able to review a patient's chart. At times, the physician isn't even aware of contraindications for certain medication because tests revealing those contraindications have not been performed or had not been recorded in a patient's chart. In some instances, even though contraindications for certain medications are documented, the physician simply fails to detect the contraindications from the patient's chart. Consequently, some oversight is needed in order to determine if mistakes are made or if an ADE might occur in a patient's medication regimen.

Since a pharmacy department of a medical facility is typically responsible for filling all prescriptions and dispensing all medications to patients, it is often the only means for catching some of these errors. To that extent, some pharmacies have information systems in place that can alert the pharmacist that an ADE would occur between drugs administered to a patient. However, these information systems are typically limited to detecting a potential ADE between drugs administered to a patient. These pharmacy information systems are not capable of predicting an ADE based on a patient's physiological condition, because these systems typically do not monitor or have access or have the capability to process a patient's laboratory results.

A laboratory department of a medical facility typically performs tests and analyzes specimens (such as blood, urine, cell cultures, etc.) received from a patient and stores these results on a laboratory information system. In many instances, the test results and analysis on patient specimens are germane to the administration of medication. However, despite this symbiotic relationship between the laboratory and the pharmacy, these two departments and their work processes, personnel, and particularly their information systems, rarely effectively communicate with each other.

In many clinical settings, there are a number of factors which prevent the integration of data from the laboratory and the pharmacy. Compatibility issues between the separate information systems is often a major roadblock to integration. The desire of each department to have information systems particularly adapted for their respective needs may be another. The cost of integrating data from both information system is certainly another prohibiting factor. As a result, there is a need for a commercial system that integrates and uses laboratory and pharmacy data to anticipate potential ADEs in a patient's medication regimen.

Thus, significant improvements in patient care can be achieved by developing a cost effective, commercial, turnkey system that integrates data collected and stored in pharmacy and laboratory information systems and utilizes this data to anticipate potential ADEs in a patient's medication regimen.

BRIEF SUMMARY OF THE INVENTION

The present invention is a system and method for anticipating potential ADEs in a patient's medication regimen by integrating data typically located in laboratory and pharmacy information systems and filtering the data using predefined criteria. The present invention includes a system for anticipating a possible ADE through the use of a search engine that compares integrated data from laboratory and pharmacy information systems and compares it to predefined ADE rules defining normal ranges for a particular laboratory test. If an abnormal test value is received and a drug in the patient's medication regimen satisfies a drug included in an ADE rule then an alert procedure is triggered which allows for a period of time wherein the patient's lab and pharmacy data is monitored in order to determine if a proper corrective action is undertaken, and if no corrective action or an improper corrective action is taken within that period of time, the healthcare provider is warned of a potential ADE.

In one embodiment, the ADE monitoring system is utilized in an application service provider environment (ASP) wherein the ADE monitoring system is comprised of at least one server having a communication link to a computer network. In this embodiment, a secure intranet provides the conduit through which data is downloaded from the medical facility, and users access the ADE monitoring system.

In another embodiment, a method for detecting an ADE is disclosed which includes extracting information within pharmacy and lab data and respectively placing it into a normalized drug table or a normalized lab table. The data within these tables are then filtered by an ADE search engine which searches an ADE rule database to see if it matches any predefined ADE rule. If a match is made an alert procedure is activated.

While several embodiments are disclosed, still other embodiments of the present invention will become apparent to those skilled in the art from the following detailed description. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE ATTACHMENTS

FIG. 7 is an embodiment of an ADE rule.

FIG. 8b is a continuation of FIG. 8a.

FIG. 15a is an embodiment of a patient table.

FIG. 16 is an embodiment of a patient alert.

FIG. 19a is an embodiment of a rule maintenance screen.

FIG. 19b is a continuation of the screen of FIG. 19a.

DETAILED DESCRIPTION OF THE INVENTION

The subject invention is a system and method for monitoring patient—drug/lab interactions by integrating data typically located in laboratory and pharmacy information systems and comparing it to predefined ADE rules. It is also contemplated that physiological data (such as blood pressure or heart rate) or patient information, obtainable from computer systems within a health care facility, can also be integrated into the disclosed invention in a manner similar to that described for the pharmacy and laboratory systems.

As will be explained in greater detail below, the subject invention includes a system configuration which facilitates data transfer, a data import procedure which integrates laboratory and pharmacy data, an ADE monitoring procedure which performs an extensive search for potential ADE, an alert generation procedure for notifying medical facilities of potential ADE, report generating functions for arranging the display of data, and a user interface which allows for simple operation of the ADE monitoring system.

A. System Configuration

Figure 1:
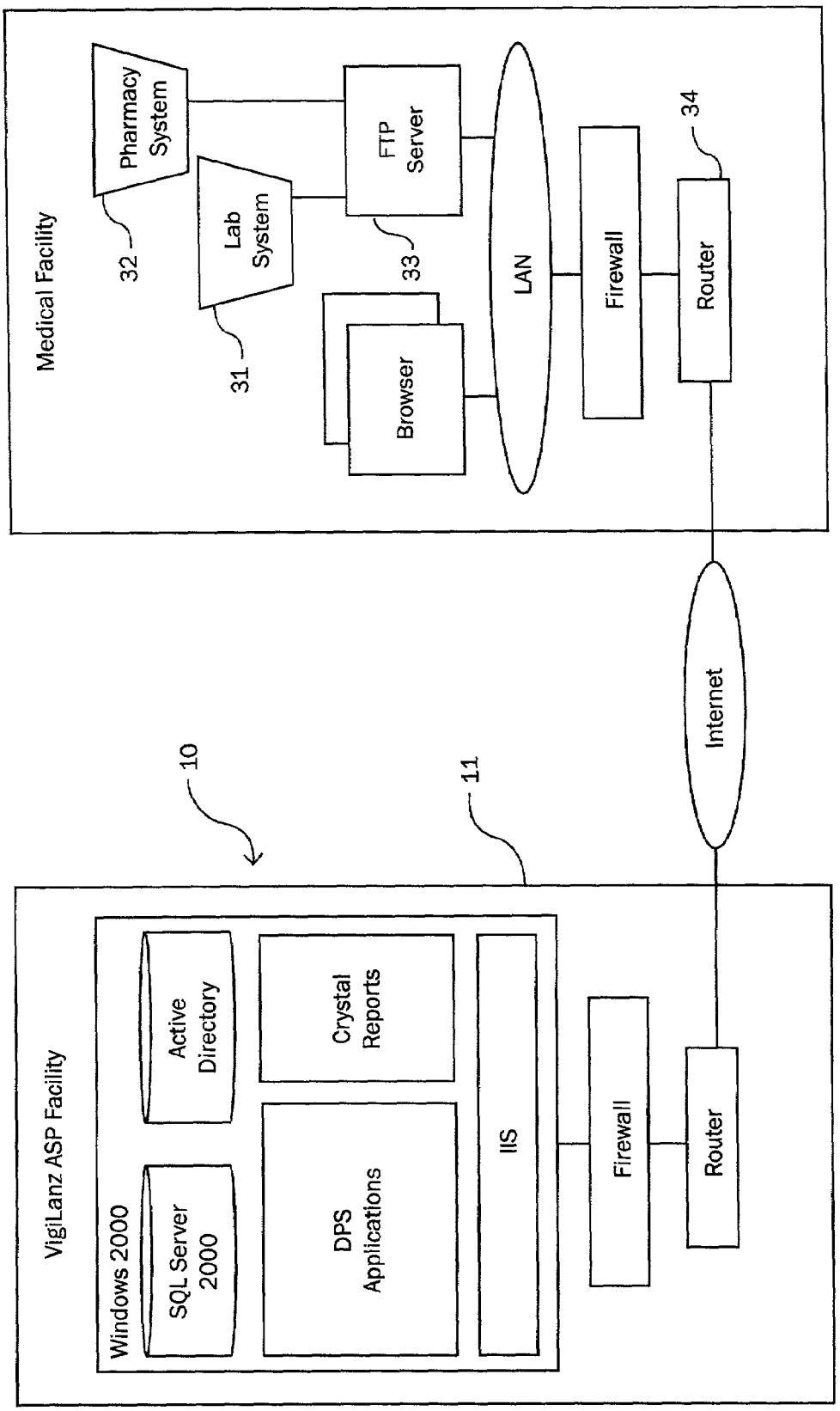
FIG. 1 is a block diagram representing an embodiment of an ADE monitoring system in an application service provider environment.
Figure 2:
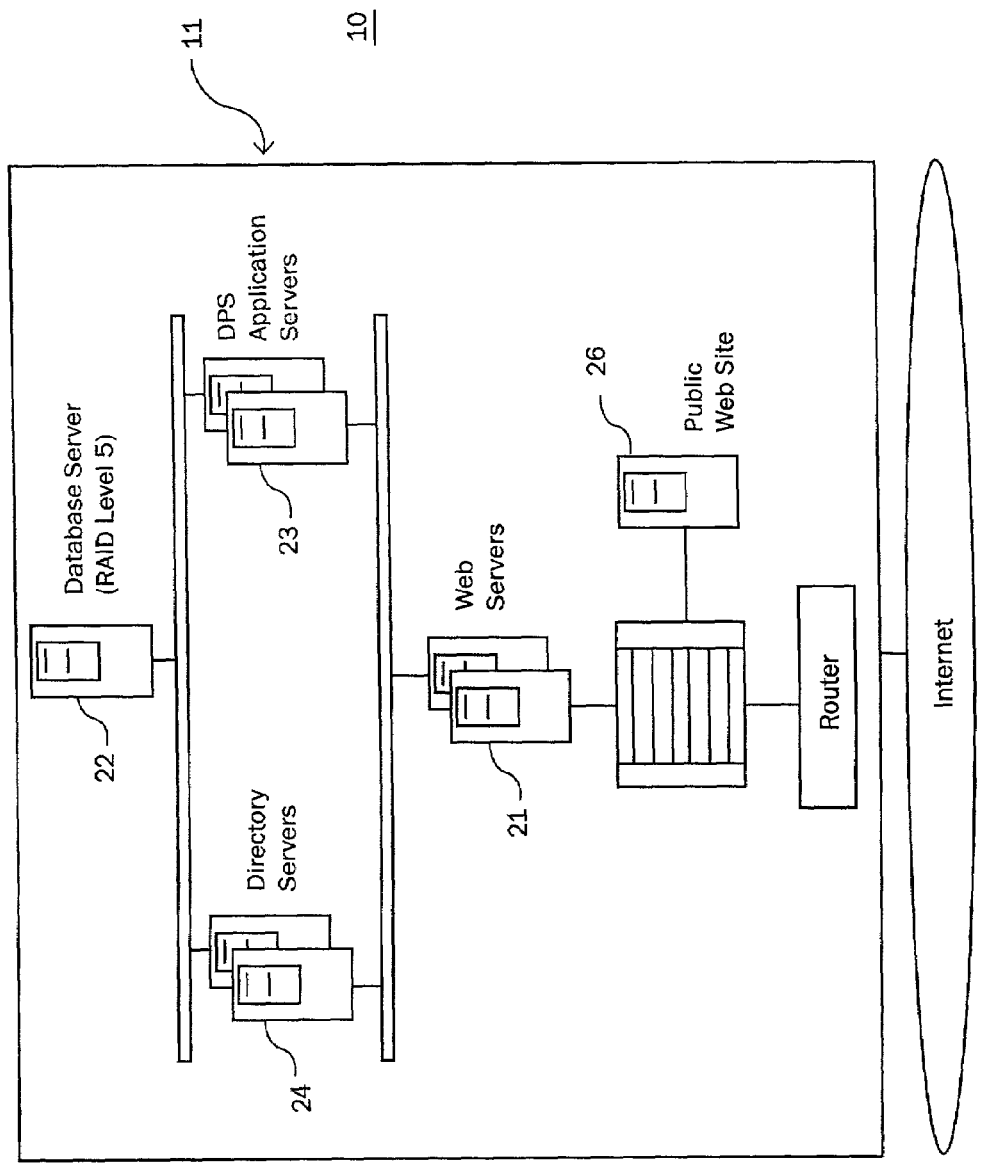
FIG. 2 is a diagram representing the hardware components of the ADE monitoring system of FIG. 1.

As shown in FIGS. 1 and 2, an embodiment of an ADE monitoring system 10 in accordance with the subject invention is shown. This embodiment is comprised of a central processor 11 having included therein a number of task oriented applications. The central processor 11 can be any computer known to those skilled in the art, including standard attachments and components thereof (e.g., a disk drive, hard drive, CD/DVD player or network server that communicates with a CPU and main memory, a sound board, a keyboard and mouse, and a monitor). The processor of the CPU in the computer may be any conventional general-purpose single- or multi-chip microprocessor. In addition, the processor may be any conventional special purpose processor such as a digital signal processor or a graphics processor. The microprocessor can include conventional address lines, conventional data lines, and one or more conventional control lines.

As shown in FIG. 2, in one embodiment, the ADE monitoring system 20 is utilized in an application service provider environment ("ASP") accessible to a plurality of users and medical facilities through a secure intranet. In this embodiment, the central processor 11 includes a web site hosted by at least one web server 21 in communication with the intranet. The central processor 11 may also include a plurality of web servers 21, database servers 22, application servers 23, or directory servers 24, and may run on a variety of platforms known in the art, including but not limited to, SQL Server 2000, Windows 2000, Active Directory and IIS.

Figure 3:
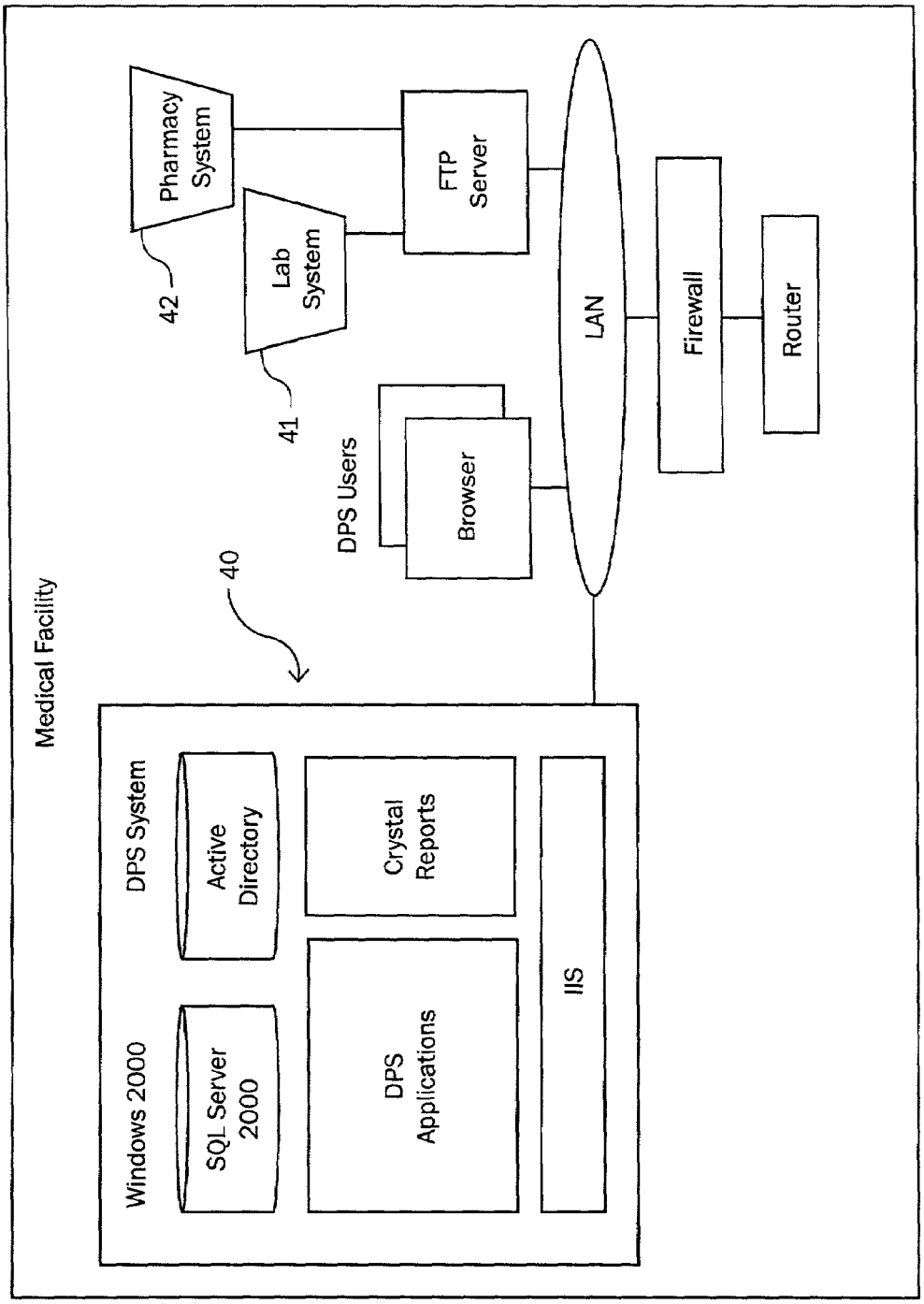
FIG. 3 is a block diagram representing an alternative embodiment of an ADE monitoring system in a stand-alone environment.

As shown in FIG. 3, in another embodiment, the ADE monitoring system 30 is configured to operate in a stand-alone environment, located within a medical facility. Data from laboratory 41 and pharmacy 42 information systems may be compiled and transmitted by a FTP server 43 through a Local Area Network (LAN).

As shown in FIGS. 1 and 3, data from laboratory 31 and pharmacy 32 information systems may be compiled and transmitted to the ADE monitoring system 10 by a File Transfer Protocol ("FTP") server 33 through a router 34 in communication with the ADE monitoring system 30 via a computer network such as a secure intranet or a LAN. In other embodiments, telephonic means or even direct hard wire connections can be utilized for transmitting data to the ADE monitoring system 10. The data transfers are typically initiated by a medical facility, and can be transmitted periodically or may be transferred dynamically as the data is created. In one embodiment, the data is encrypted prior to transmission to secure the privacy of the information.

Figure 4:
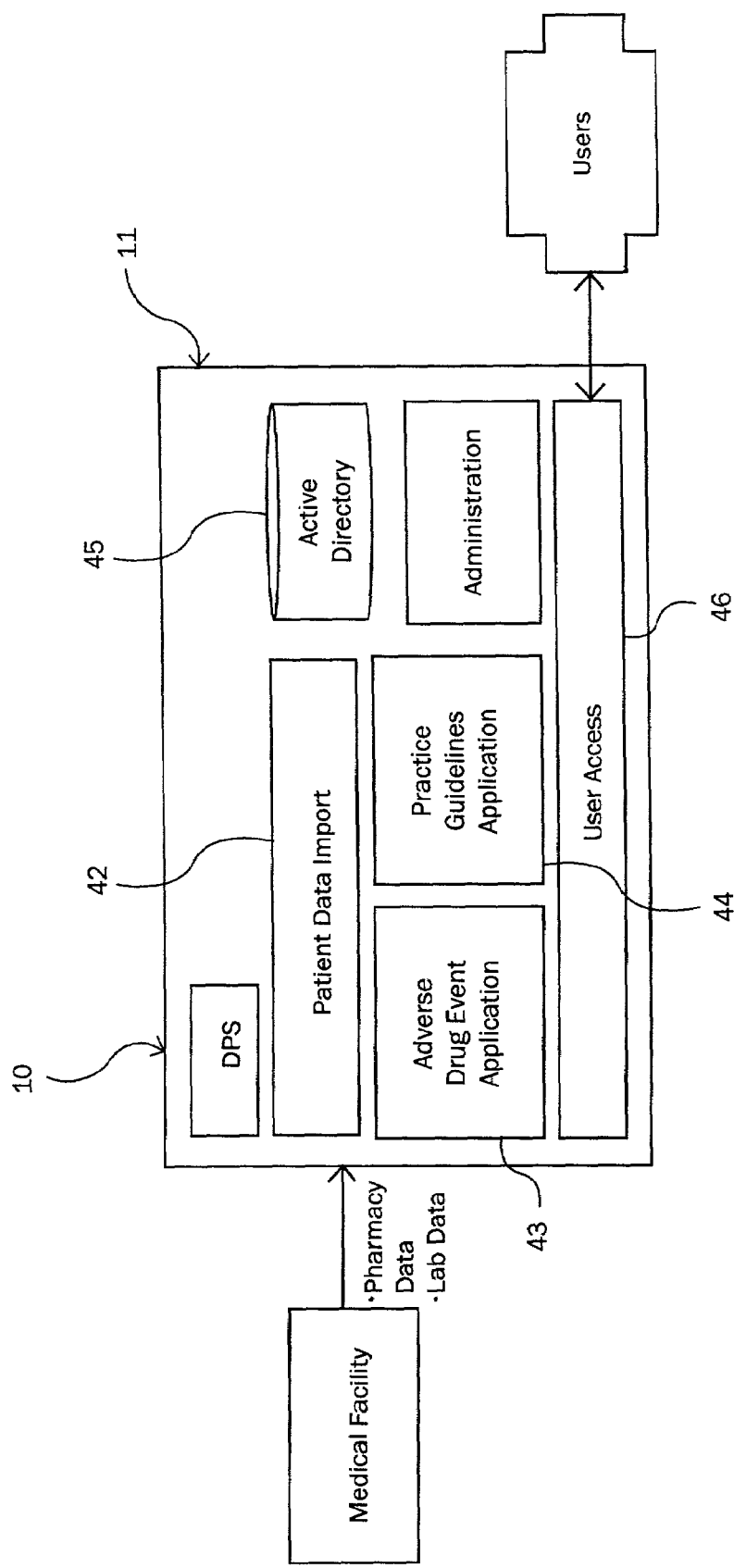
FIG. 4 is a diagram representing an embodiment of the ADE monitoring system.

As shown in FIGS. 1, 2, and 4, in one embodiment, the central processor 11 includes software applications or computer instructions located on application servers 23. As will be explained further below, and more specifically in the sections pertaining to their function, the applications coordinate the functional components of the ADE monitoring system 10. These applications may include common software components that are commercially sold, as well as proprietary applications specifically developed to perform specific functions in the ADE monitoring system.

A Patient Data Import Application 42 is included to receive, validate, and format pharmacy and lab data received from a medical facility. An Adverse Drug Event Application 43 is included to correlate and examine pharmacy and lab data for each patient, and to generate an alert when these criteria do not comply with predefined criteria. A User Access Application 46 may also be included for limiting access to the ADE monitoring system 10 to authorized individuals and for limiting access to information. The User Access Application typically works in conjunction with a User Directory 45 located on a directory server 24. The User Directory 45 is comprised of a database of authorized users and a level of accessibility allowed for each. An Administration Application may also be included for organizing and maintaining databases pertaining to particular medical facilities and users. A report generation application such as Crystal Reports may also be included.

B. Importing Data

Figure 5:
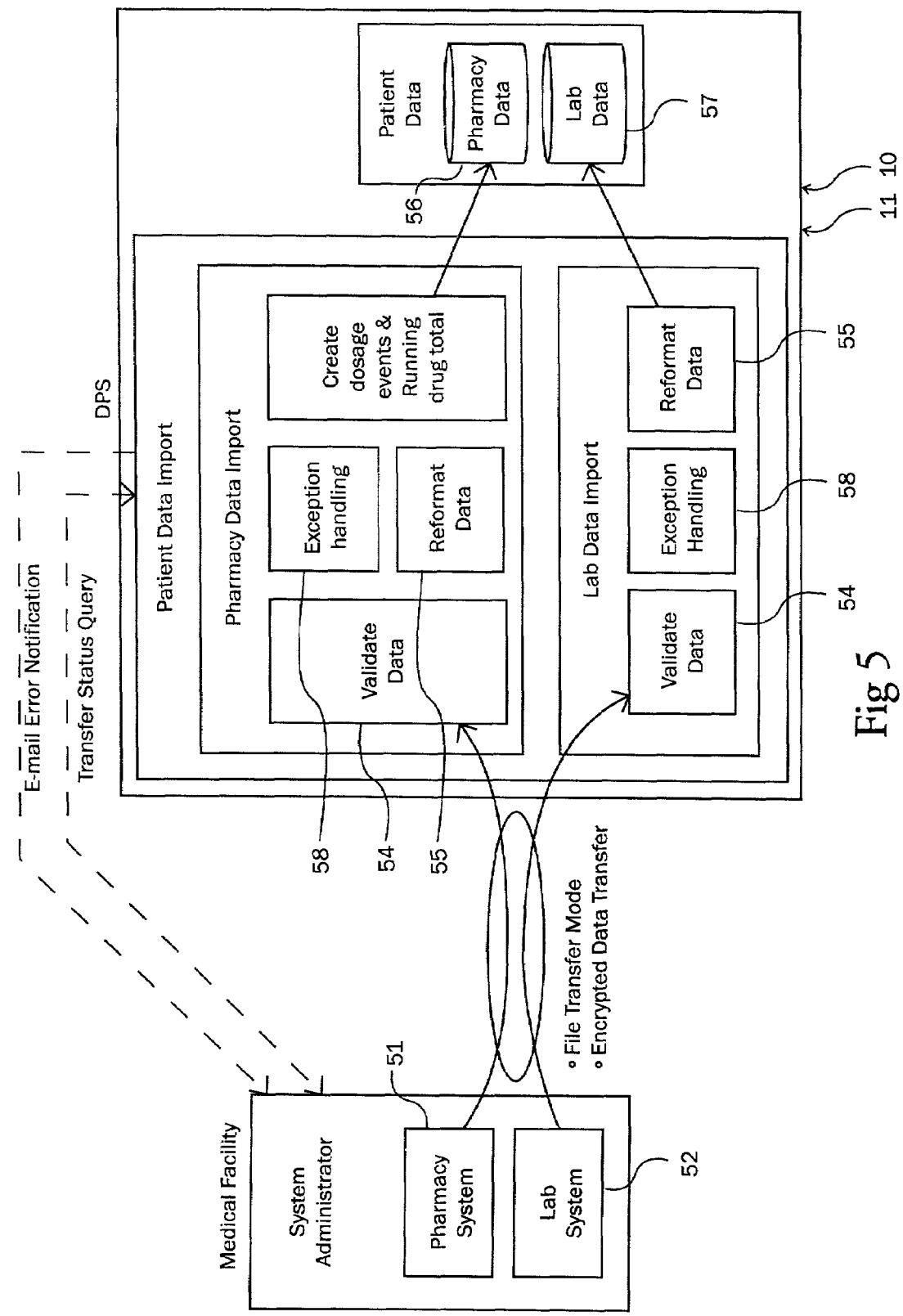
FIG. 5 is a block diagram representing an embodiment of a data import procedure.
Figure 6:
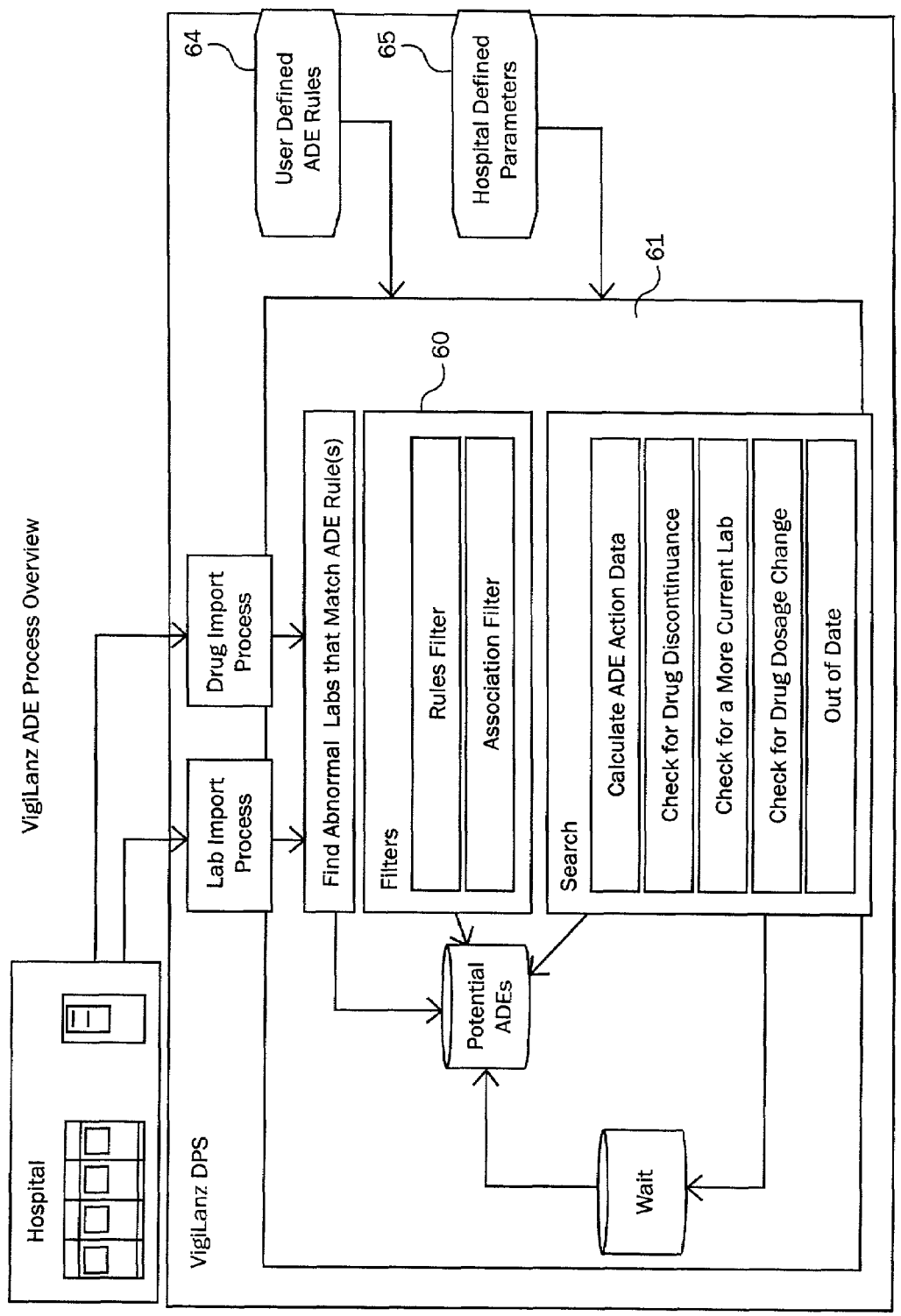
FIG. 6 is a block diagram representing an embodiment of an ADE monitoring procedure.

As shown in FIGS. 5 and 6, in one embodiment, data records from a healthcare facility is transmitted to the ADE monitoring system through a secure intranet. The ADE monitoring system 10 first subjects the data record to a validation process (block 54) to verify that the data record is in a known format and to verify that it is complete. Once the data record is verified, it is then reformatted by a reformatting process (block 55) to be compatible with data structure employed by a database wherein the data is stored.

If an error occurred in the transmission of the data record or if the data record is improperly formatted, an exception handling procedure (block 58) is triggered. The exception handling procedure (block 58) includes the steps of creating an error message and posting it on an error log which notes the time and date of the error. Also, an electronic message, preferably an E-mail, is sent to the healthcare provider sending the data record to notify it of the error.

A pharmacy information system 51 will typically provide the ADE monitoring system 10 with pharmacy data for each patient and a laboratory information system 52 typically provides information pertaining to lab tests. A data record imported from a pharmacy information system will typically include information pertaining to a medication prescribed to a patient and the logistics as to how the medication is to be administered. A data record from a lab information system typically provides data pertaining to lab tests for each patient. Lab or pharmacy data is extracted from their respective data records and this data is then correlated with records pertaining to the same patient ID, and stored within a database. In this embodiment, a pharmacy database 56 stores pharmacy data and a laboratory database 57 stores laboratory data.

The data record can be an ASCII file or it can be formatted in any known manner. A pharmacy data record will typically include data fields containing a patient ID, a doctor ID, the drug administered, a dosage, a time of dosage, a begin date, and a discontinuance date. A lab data record will typically include data fields for a patient ID, a doctor ID, a lab test performed, the test result, the date and time of the test.

In one embodiment, a normalized table called a daily record is created from data extracted from a pharmacy data record and stored within the pharmacy database 56. The table is comprised of a chronological sequence of records, with each record having data fields identifying a drug, a drug dosage given or to be given, and a time and date when the drug dosage is administered or will be administered. Each record also includes a data field which represents the total dosage for a particular drug within a 24 hour period from the time the drug is or will be given. A new record is created with each drug dosage given or each drug dosage to be given, and the daily record is updated with each new record.

A normalized lab table is also created from lab data and stored within the laboratory database 57. The table is also comprised of a chronological sequence of data records, with each data record having data fields identifying a patient ID, a time of the test, the lab name, and the lab result. A new record is created for every test result, and the lab table is updated after the creation of each new record.

C. ADE Rules

As shown in FIG. 6, prior to the use of the ADE monitoring system, ADE rules 64, 65 are created and stored within the ADE rule database 60. Each ADE rule contain a plurality of data fields therein which contain information that is used by the ADE monitoring system to determine if an ADE has occurred. The values which are contained in each data field are either defined by or approved by a healthcare provider utilizing the ADE rules. These ADE rules can include some created by a service which provides ADE monitoring 64 and some created by the medical facility 65.

As shown in FIG. 7, an ADE rule is a data record that includes a plurality of fields. In one embodiment, an ADE rule includes data fields for search status 71, search type 72, target drug 73, target lab 74, drug lab/search name 75, severity 76, lab code 77, pattern 78, type 79, baseline 80, absolute 81, interval 82, danger multiplier 83, momentum multiplier 84, allergy 85, hospital unit 86, doctor(s) 87, diagnosis 88, gender 89, age range 90, concurrent drugs 91, concurrent labs 92, alert template 93, description 94, and contact 95. A precursory explanation of the contents of each field are defined below, the functions of these fields will be expanded further in the specification when needed to describe the functionality of the subject invention.

Search Status 71 determines if a rule is to be used when performing ADE monitoring. If enabled the rule is used by the subject ADE monitoring system.

Search Type 72, Drug/Lab Search Name, and Description 94 are all fields used to classify an ADE Rule. Search Type 72 is used to signify if an ADE rule is a research rule or an alert rule. Alerts are specifically written to produce an alert procedure when satisfied. Research rules are specifically made for research purposes only and do not need to trigger an alert procedure if satisfied. Drug/Lab Search Name 75 is a unique indentifier which represents a particular rule.

Target Drug 73 and Target Lab 74 are the drug and lab combination which is the focus of an ADE rule. Target Drug 73 names the drug which is the basis for the rule. Target Lab 74 names the lab test which is the basis for the rule.

Severity 76 indicates the severity of the ADE.

Lab code 77 is a unique identifier for the Target Lab 74.

Pattern 78 specifies whether the rule is looking for a high or low lab test, and what is the normal drug response to the lab test (i.e. whether to raise or lower the drug dosage.).

Type 79 and Baseline 80 are data fields used to determine if a lab value is abnormal. Type 79 specifies whether the Baseline value 80 defines a high border or a low border of a normal lab result. Baseline 80 represents a value that exceeds or fails to reach either a maximum or minimum normal value, respectively, for the Target Lab 74.

Absolute 81, Interval 82, Danger Multiplier 83, and Momentum Multiplier 84 are all used to determine an appropriate waiting period wherein a corrective action is to be taken. Absolute 81 represents a lab test value that is considered dangerous. If the test value in a Drug/Lab data record is equal to or exceeds the Absolute 64 value then the ADE monitoring system treats the situation as a medical emergency. Interval 82 in the ADE rule contains the time interval (in hours) within which the ADE monitoring system expects an action to occur. The Danger Multiplier 83 contains a variable that automatically adjusts how quickly the ADE monitoring system expects a response to an abnormal lab test, based upon how close the lab test is to an Absolute 81 value. Momentum Multiplier 84 includes a factor that takes the previous lab value into consideration and automatically adjusts the Interval accordingly.

Allergy 85 indicates an allergic reaction to a particular drug. This parameter is simply enabled or disabled. Once enabled and if the baseline value is reached or exceeded, the only action capable of removing an alert would be the discontinuance of the Target Drug 73. This parameter does not depend on a history of allergy by the patient but is a link with a particular lab test and result that can indicate that the patient is allergic to the drug.

Hospital Unit 86, Doctor 87, Diagnosis 88, Gender 89 and Age Range 90, if defined, are additional requirements that must be satisfied if an alert procedure is to be triggered. These parameters are referred to as detail filters and they represent specific conditions which, if present, will override the continued processing of an abnormal lab condition.

Concurrent Drug 91 and Concurrent Lab 92 are associated conditions which must be present for an alert procedure to be triggered and are referred to as association filters. Concurrent Drug 91 names medications that must have been administered to a patient within a prescribed period of the abnormal lab for an alert condition to exist. Similarly, Concurrent Lab 67 lists additional tests and test values that must be present within a prescribed period of the abnormal lab before an alert procedure is triggered.

Alert Template 93 and Contact 95 are used in sending an alert to a healthcare provider. The Alert Template 93 contains the name of a template which defines how to handle an alert for the specific ADE rule and Contact 95 lists who should be contacted if an alert is sent.

D. ADE Monitoring

As shown in FIG. 6, in one embodiment, ADE monitoring is performed by receiving data from a healthcare provider's laboratory and pharmacy information systems and integrating and correlating the data. This data is then submitted to an ADE search engine 61 which searches an ADE rule database 60 to see if the data satisfies any predefined ADE rule. If a definition is satisfied, an alert procedure is activated to notify the medical facility of a potential ADE.

ADE monitoring can be done in real time by having the medical facility transmit applicable data as soon as it is received, and by having ADE monitoring activated automatically upon reception of new laboratory and pharmacy data. Real time ADE monitoring allows nearly instantaneous detection of ADE. The ADE monitoring system can also be activated periodically by allowing transmitted pharmacy and lab data to accumulate in pharmacy 56 and laboratory 57 databases and searching for matches at predefined times, or upon activation by a user.

Figure 8A:
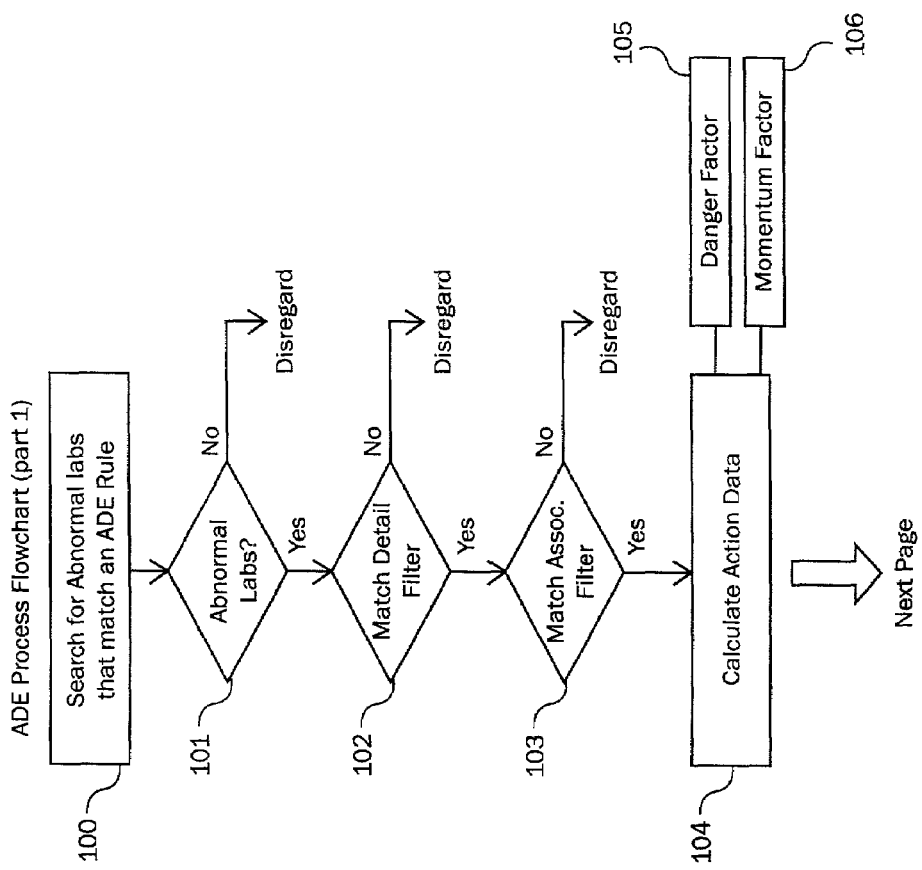
FIG. 8a is flow chart representing the ADE monitoring process.
Figure 9:
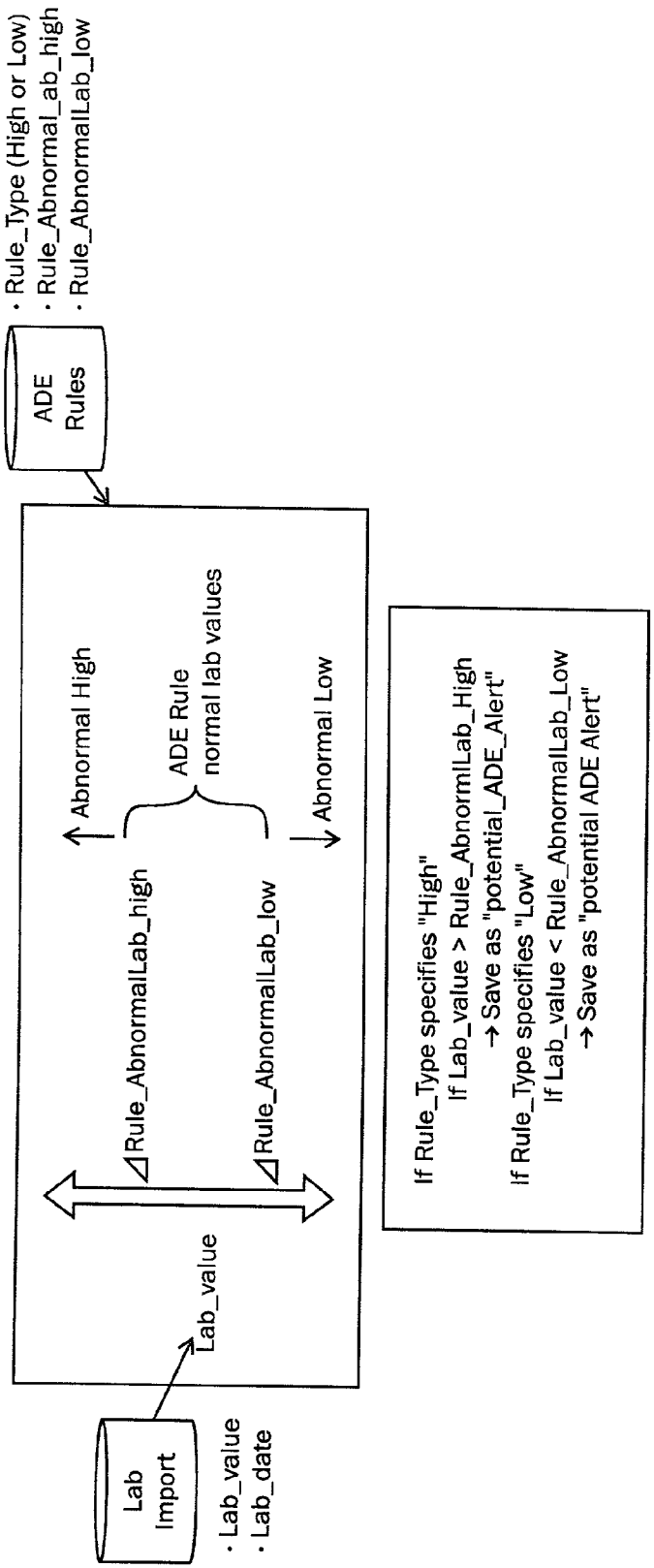
FIG. 9 is a diagram depicting detection of an abnormal lab result.

As shown in FIGS. 8a and 9, in one embodiment, once ADE monitoring is activated, the subject ADE monitoring system will first check to see if an abnormal lab is received (box 100). This check is done by filtering data located within the pharmacy 56 and lab 57 databases with the plurality of ADE rules stored within the ADE rules database to see if an ADE rule is satisfied by the pharmacy and lab data.

The filtering process includes using the lab name stored within the Target Drug 73 data field of an ADE rule to filter the drugs listed in the daily record to determine if it was administered or is scheduled to be administered to a patient during a predefined period. If a match exists, the records within the lab table is then filtered using the data located within the Target Lab 74, Baseline 80, and Type 79 data fields located in the same ADE rule to determine if an abnormal lab result has been received.

As shown in FIG. 9, if a lab name located within the Target Lab 74 data field matches a lab name in the lab table, then the value for the lab is compared with the value within the Baseline 80 database for the same ADE rule. If the lab value is equal to or exceeds (if Type 79 is high) or if it does not exceed (if Type 79 is low) the value in the Baseline 80 data field, then the lab value is an abnormal lab. After an abnormal lab result is detected and absent any additional criteria in the detail filters or association filters, an ADE rule has been satisfied and an alert procedure is triggered.

Figure 11:
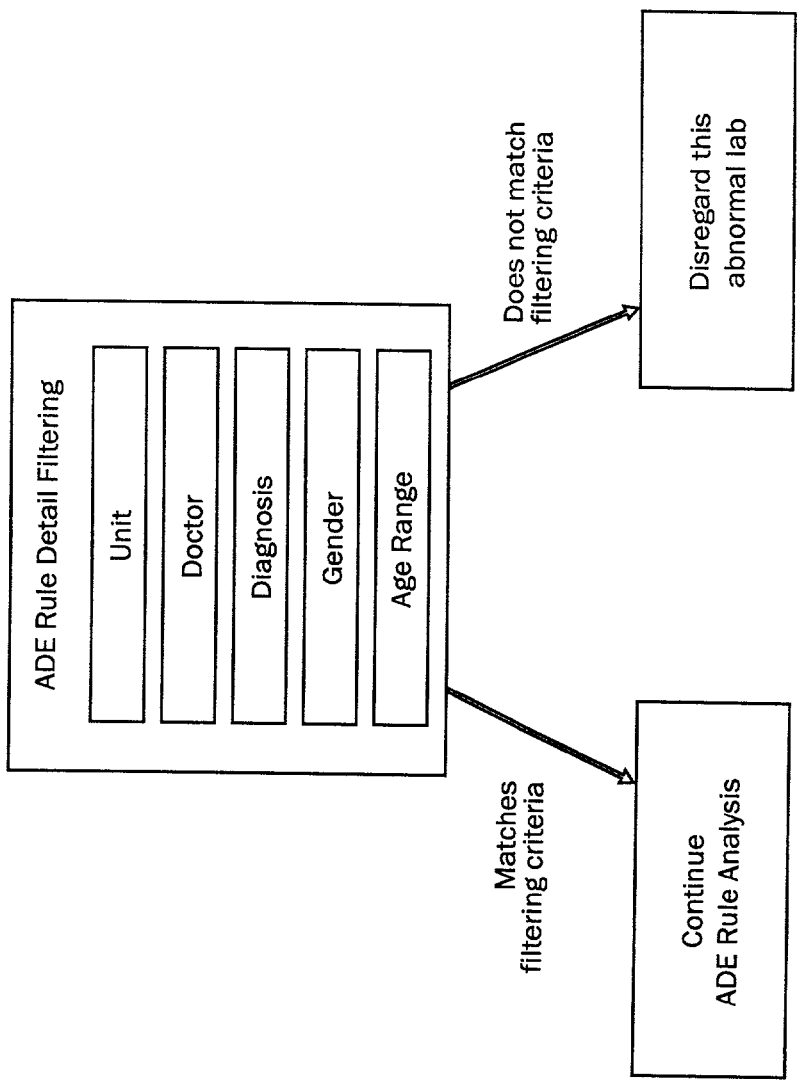
FIG. 11 is a diagram depicting filtering for specific details.

As shown in FIG. 11, the data fields Hospital Unit 86, Doctor 87, Diagnosis 88, Gender 89 and Age Range 90, comprise a detail filter that, if defined, are additional requirements that must also be satisfied if an alert procedure is to be triggered. If a drug/lab match exists then the patient record is checked to see if the defined detail filters are satisfied (Box 102). If any defined detail filters are not satisfied, then the drug/lab match is disregarded.

Figure 10:
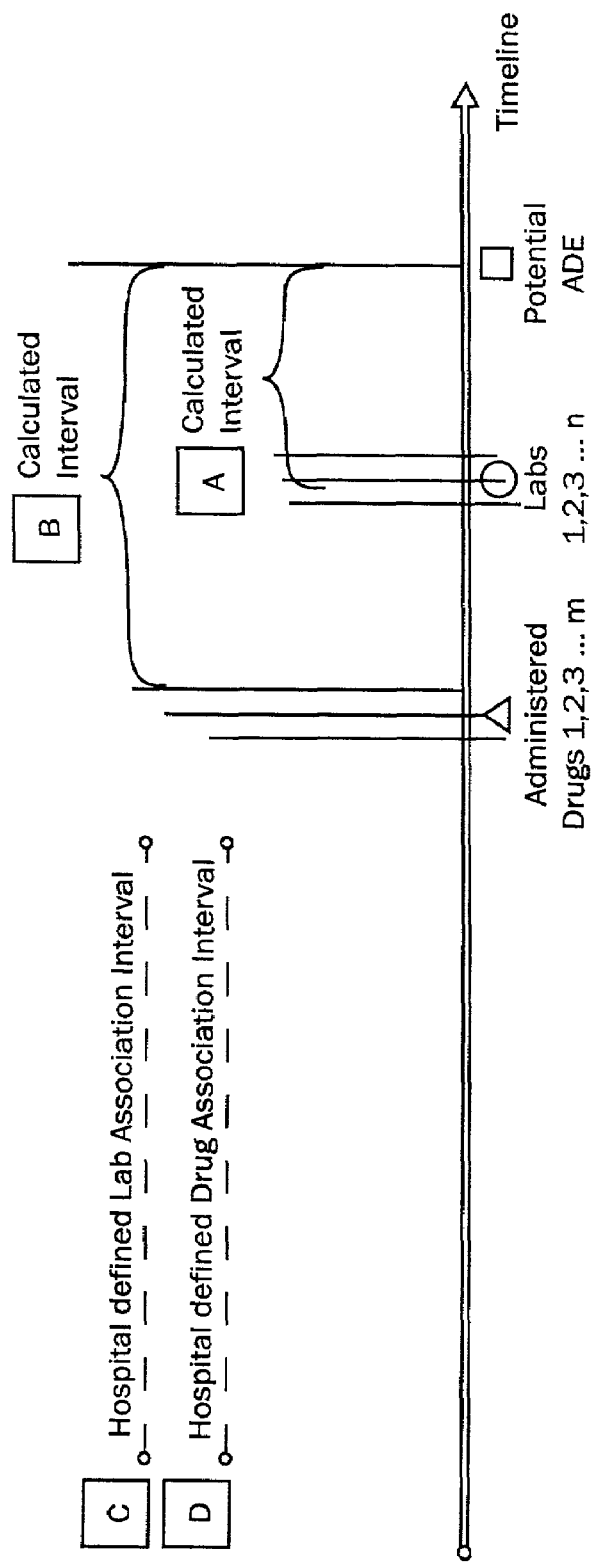
FIG. 10 is a diagram depicting concurrent lab and drug features.

If a drug/lab match is found and the detail filters are satisfied, the search engine then checks the Concurrent Drug 91 and Concurrent Lab 92 data fields to see if these association filters are defined (Box 103). As shown in FIG. 10, if any of the association filters are defined, the search engine filters through the daily record or the lab table, depending on which parameter is defined, to see if the associated drug was administered or if the associate lab result occurred within a predefined period of time prior to the abnormal lab result. If the association filter is satisfied, then the ADE monitoring system can begin an alert procedure. If they are not, then the drug/lab match is disregarded.

E. Alert Procedures

Figure 8B:
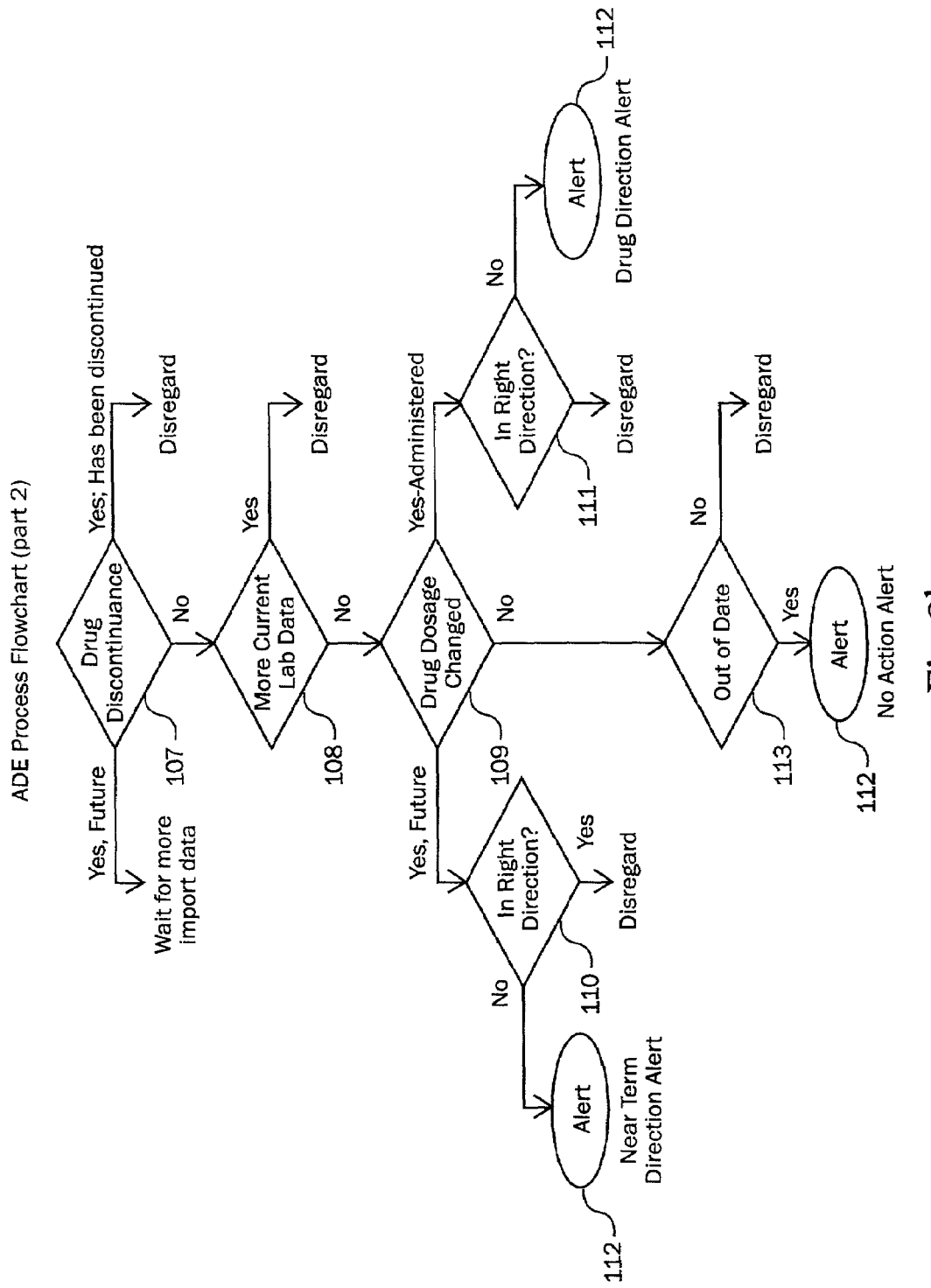

As shown in FIGS. 8a and 8b, in one embodiment, an alert procedure includes calculating an action date (box 104) which defines a waiting period wherein the system allows the problem to be resolved by the medical staff and allows time for additional tests to ensure that a potential ADE does exist (the abnormal lab value being erroneous). The action date is adjusted (boxes 105 and 106) to take into account a plurality of factors such as the current abnormal lab value, the previous lab value, the amount of time between a previous lab and the current abnormal lab, and the value of a current abnormal lab relative to a potentially dangerous value for the lab.

During this waiting period prior to the action date, the system monitors incoming pharmacy and laboratory data in order to determine if a proper corrective action is taken. The proper corrective action can be discontinuing a medication or receiving a more recent test result or it can be a response such as raising or lowering a dosage (the appropriate change is listed in the Pattern 78 data field of the matched ADE rule). If the action date is reached without a proper corrective action being taken or if an inappropriate action has been taken (such as raising the drug level when it should be lowered), an alert indicating the existence of a potential ADE is generated and sent to the healthcare provider. If a proper action has been taken then the drug/lab match is disregarded.

Figure 12A:
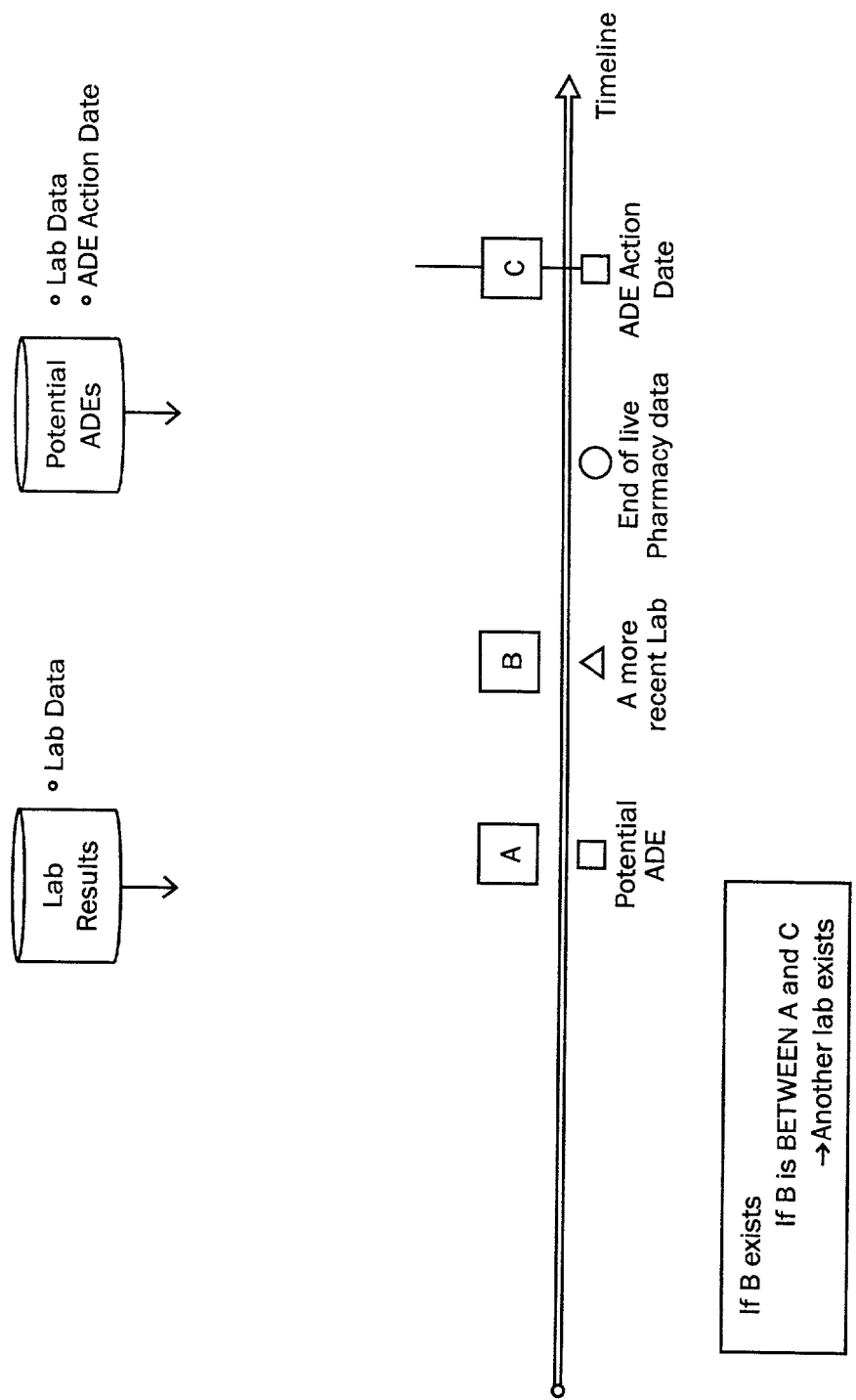
FIG. 12a is a timeline depicting a corrective action comprising of a normal lab result.
Figure 12B:
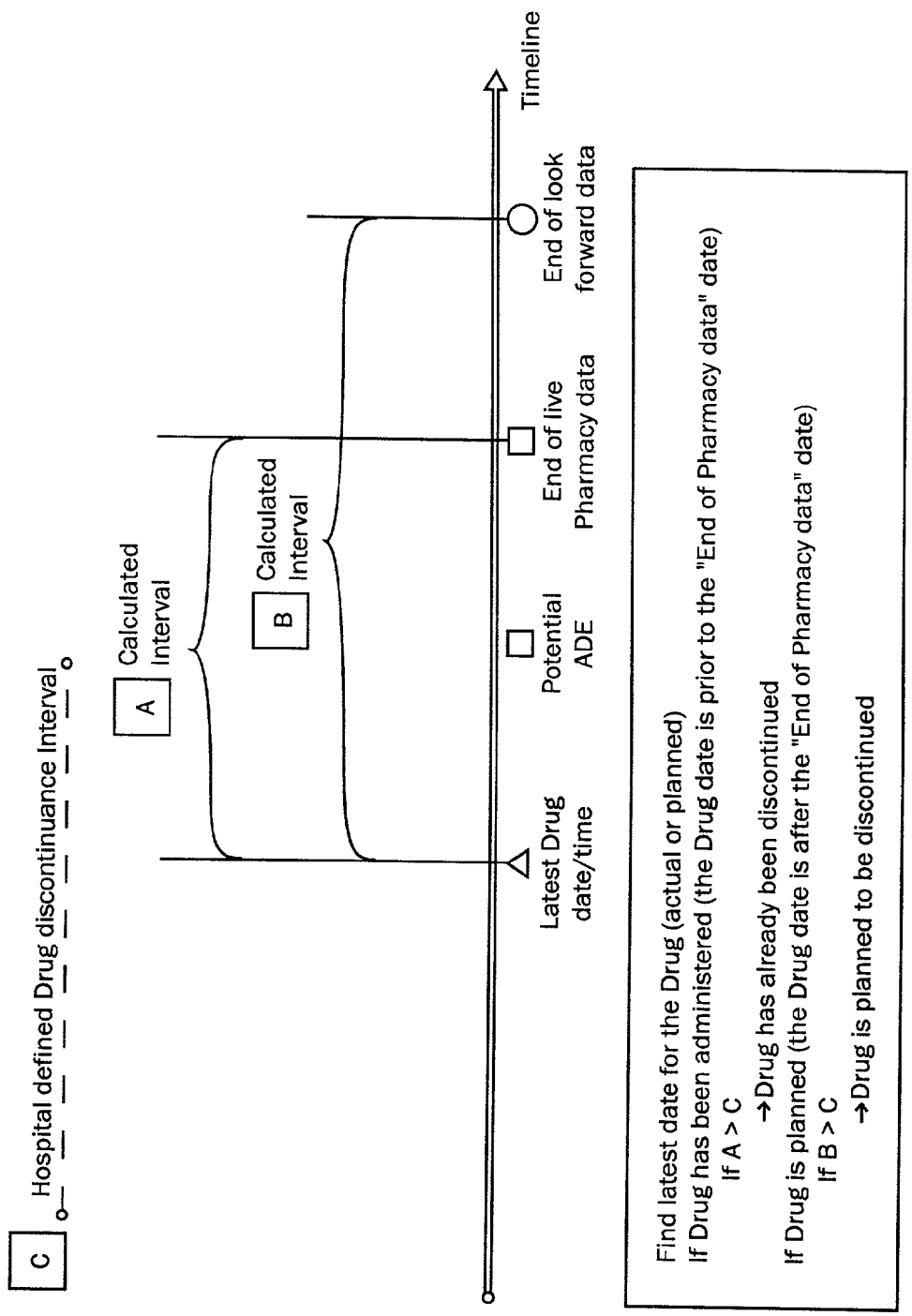
FIG. 12b is a timeline depicting a corrective action comprising of a discontinuation of a drug.

A proper corrective action can be a discontinuation of the medication (box 107). As shown in FIG. 12b, a discontinuation of a medication is detected by the ADE monitoring system by monitoring the period of time starting from the last administration of the medication to be discontinued. A time interval (C) is defined which represents a period sufficient to determine a discontinuance of a particular drug.

If the time interval between the last time a drug was administered and the end of the live pharmacy data is greater than (C), and if the drug was not administered between that time, then the drug is effectively discontinued and the drug/lab match is disregarded. If the interval (C) is not satisfied and there is no more data in the pharmacy database, the system will continue to monitor incoming lab results until the interval (C) is satisfied.

Another proper corrective action may also be receiving a more current result for the same Target Lab 74 (box 108). As shown in FIG. 12*a*, once an abnormal result (A) is received, subsequent tests are monitored to see if a more recent lab result for the same test (B) is present within the lab table. If a more recent test is present, the lab/drug match is disregarded.

Figure 12C:
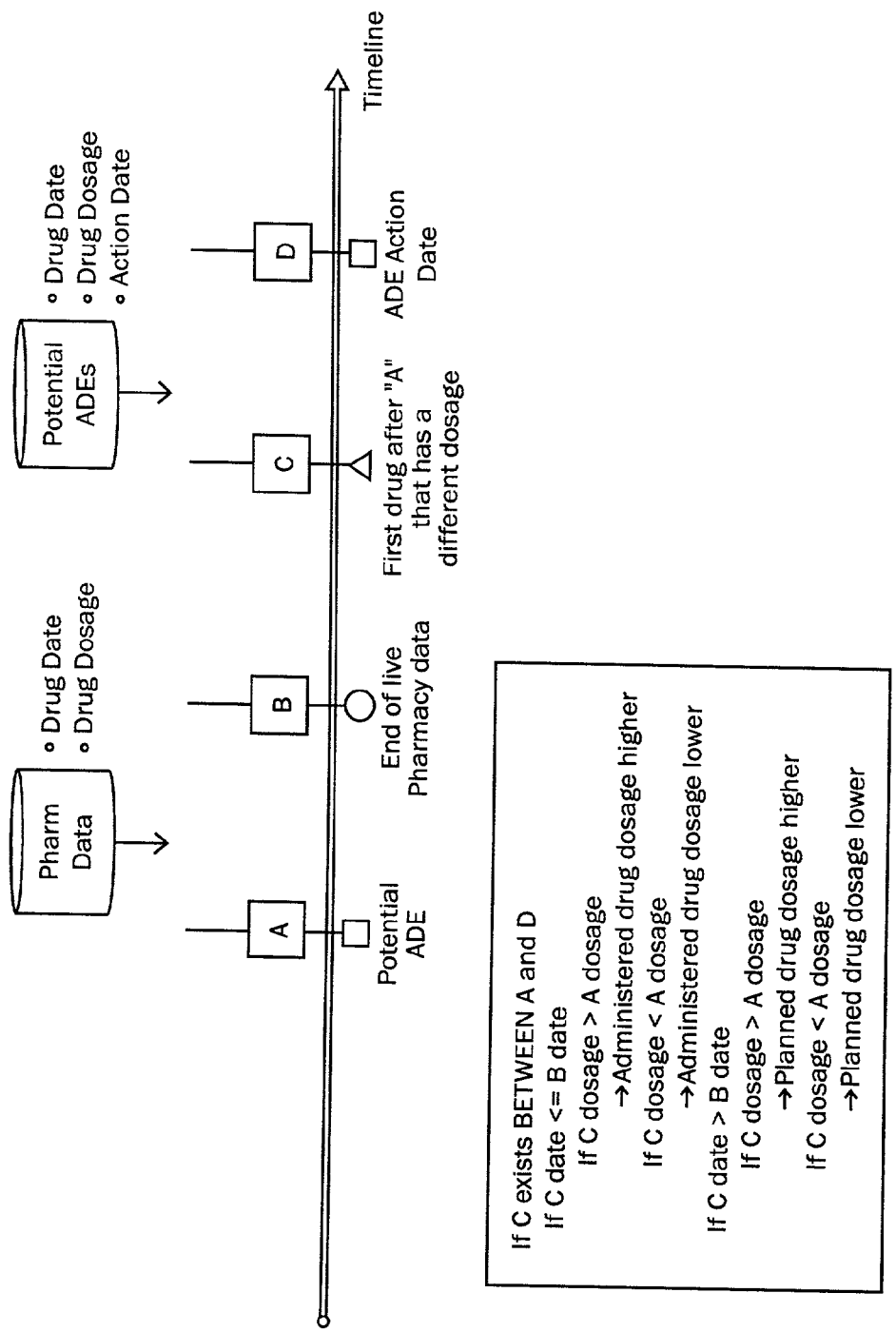
FIG. 12c is a timeline depicting a corrective action comprising of a change in dosage.

In some instances, the proper corrective action can also be an adjustment to the dosage given a patient (Box 109). As shown in FIG. 12*c*, after an abnormal lab result occurs (A) the system monitors subsequent pharmacy data to determine if an actual dosage given or planned dose (B) includes a dosage which is lowered or raised as is required by the Pattern 78 data field in the matching ADE rule. If an actual dosage or a planned dosage is properly adjusted, the drug/lab match is disregarded.

Absolute 81, Interval 82, Danger Multiplier 83, and Momentum Multiplier 84 are all data fields within a matching ADE rule that are used to determine an appropriate waiting period wherein a corrective action is to be taken. The Interval 82 data field in a matching ADE rule contains the time interval (in hours) within which the ADE monitoring system expects an action to occur, and this time period is adjusted accordingly to take into account a plurality of factors such as the current abnormal lab value, the previous lab value, the amount of time between a previous lab and the current abnormal lab, and the value of a current abnormal lab relative to a potentially dangerous value for the lab. The date wherein the interval expires and an alert is generated is called the action date. The action date is calculated by the formula:

$$\text{Action Date} = I - (DM + (AM*MF))*((I*((HV-LV0/HV-AHV))))$$

Figure 13:
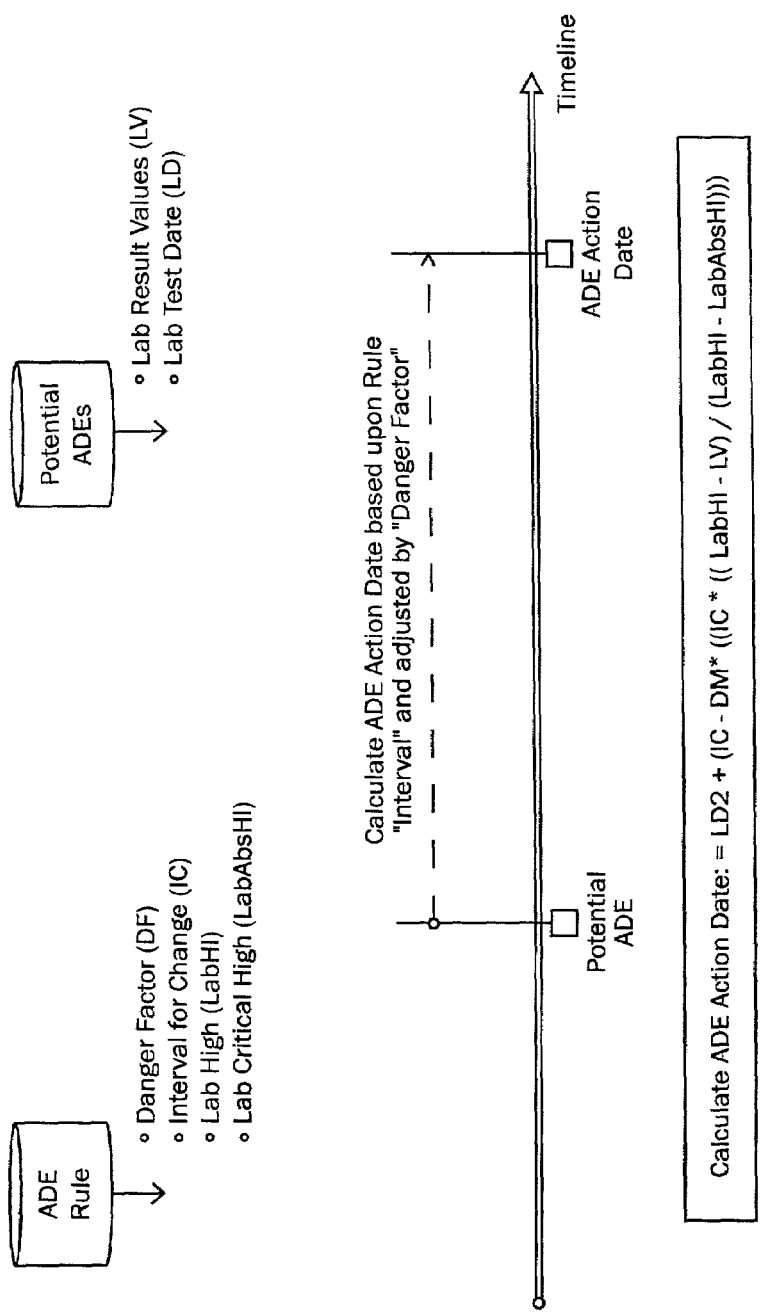
FIG. 13 is a timeline depicting an adjustment to an action date by a danger multiplier and a formula to calculate the adjustment.

Wherein:
  I—value in data field Interval 70 (FIG. 7)
  DM—represents Danger Multiplier 71
  AM—actual momentum
  MF—represents a Momentum Multiplier 72
  HV—represents the Baseline 63 value
  AHV—represents the Absolute 64 value
  LV—represents the recorded lab value The Danger Multiplier 71 contains a variable that automatically adjusts how quickly the ADE monitoring system expects a response to an abnormal lab test, based upon how close the lab test is to an Absolute 64 value. The variable is the slope of a linear function that governs how the interval time is adjusted relative to the proximity of a lab test result to the Absolute 71 value. FIG. 13 shows the formula to calculate an action date adjusted for a danger factor. The variables in the formula can be defined as:
  LD2—date of abnormal lab value
  IC—value in data field Interval 70 (FIG. 7)
  DM—represents Danger Multiplier 71
  LabHI—represents the Baseline 63 value
  LV—abnormal lab value
  LabAbsHi—represents the Absolute 64 value Momentum 72 is determined by the value given to the Momentum Multiplier (MF) by the user and the found Actual Momentum (AM). The Momentum Multiplier (MF) is set by the user much like the Danger Multiplier (DM). It acts on the Actual Momentum (AM). Actual Momentum (AM) is calculated by taking the difference in value between the current lab test and the last previous one (LV2−LV1) and dividing by the time difference between the dates of each (LD2−LD1). The value of the ratio is then corrected for the absolute value of the lab tests by dividing by the most recent lab value (LV1).

Figure 14:
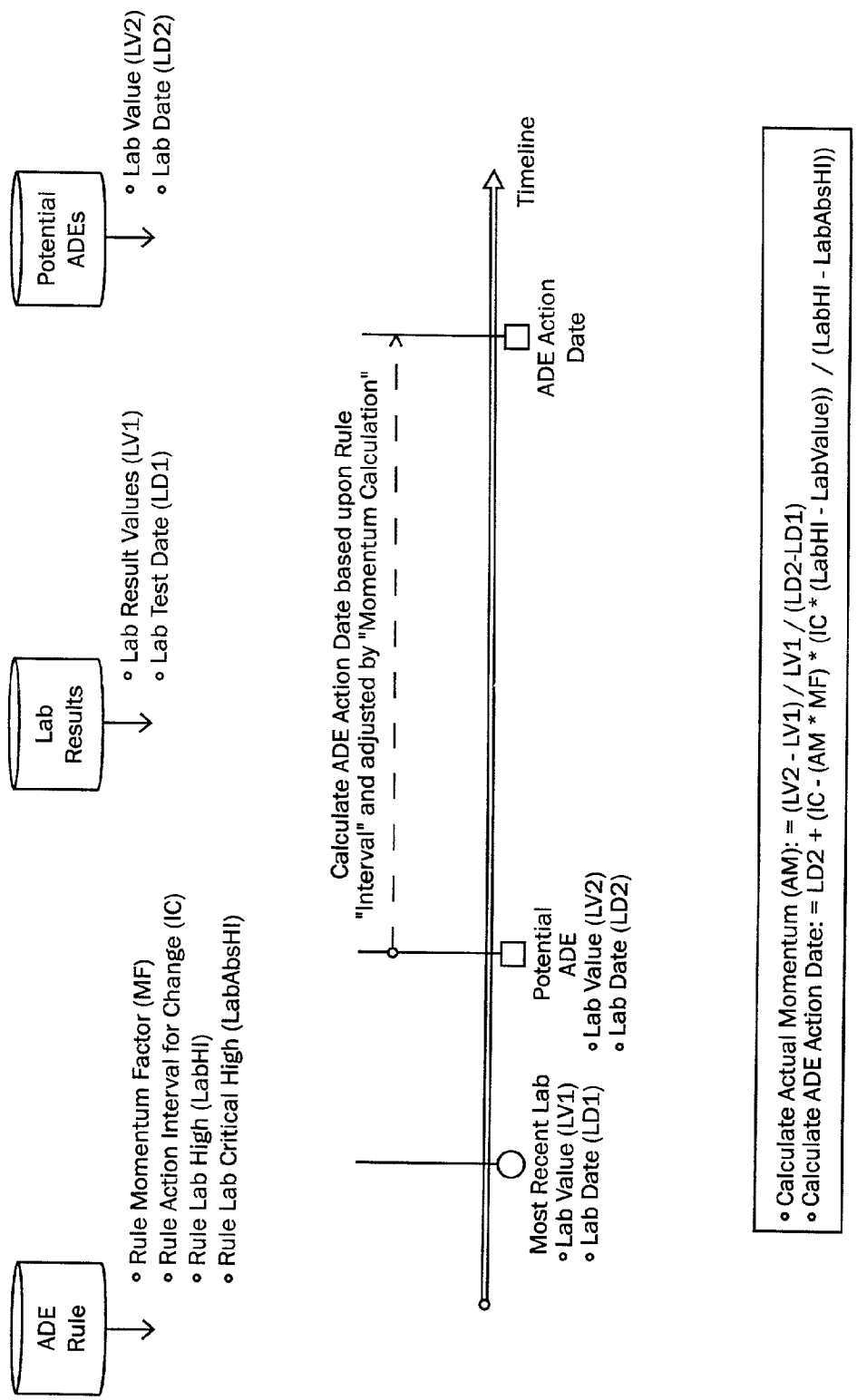
FIG. 14 is a timeline depicting an adjustment to an action date by a momentum multiplier and a formula to calculate the momentum multiplier and the adjustment to the action date.

FIG. 14 shows the formula to calculate the actual momentum and an action date adjusted by the momentum multiplier. The variables in the formulas can be defined as:
  LD2—date of abnormal lab value
  LV2—abnormal lab value (also referred to as LabValue)
  LV1—most recent lab value for same test
  LD1—most recent date for same test
  IC—value in data field Interval 70 (FIG. 7)
  AM—represents the actual momentum
  MF—represents a Momentum Multiplier 72
  DM—represents Danger Multiplier 71
  LabHI—represents the Baseline 63 value
  LV—abnormal lab value
  LabAbsHi—represents the Absolute 64 value Once an action date is reached without an appropriate action being undertaken, the system makes contact with the healthcare provider in order to alert them of a potential ADE. The matching ADE rule includes the name of an appropriate template in Alert Template 73, and a destination for the message in the Contact parameter 74. Preferably, the ADE monitoring system delivers the alert through an electronic messaging system such as an E-mail. It is also contemplated that such alerts can also be transmitted in a known manner through a paging system or a voice mail system to an attending physician. This electronic message may be received at a central point in a healthcare facility, and additionally it may be received at a nursing station located in the medical ward wherein the patient is hospitalized.

Figure 16:
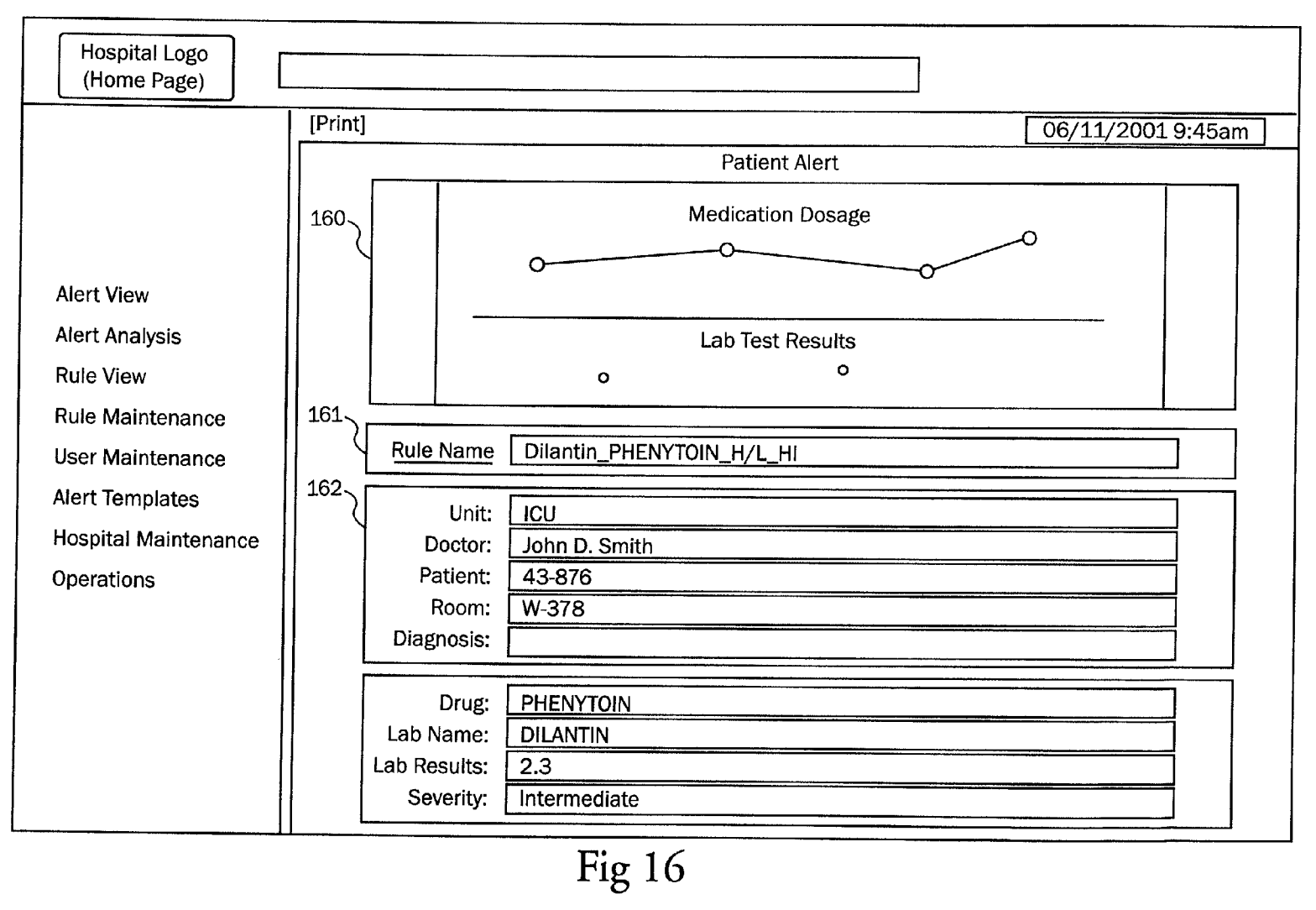

As shown in FIG. 16, one embodiment of an alert includes a graphical representation of the medication dosage relative to lab test results 160, a name of the rule satisfied, patient information 162, and drug/lab information 163. In this embodiment, the alert is a page which is located within a web site, but similar information may be transmitted to an email address, a central station within a health care organization, or a pharmacy.

F. Patient Reports

The ADE monitoring system stores data received from the medical facility as well as the alerts which are generated in a database which is accessible to users for patient care, quality assurance, or medical research. Information within the database can be filtered and compiled by a user to provide specific information relating to a particular patient or to a number of patients within a medical facility. The information can be filtered and compiled via criteria determined through an interactive query or through predefined report parameters. (need more info on report generation capability)

Figure 15A:
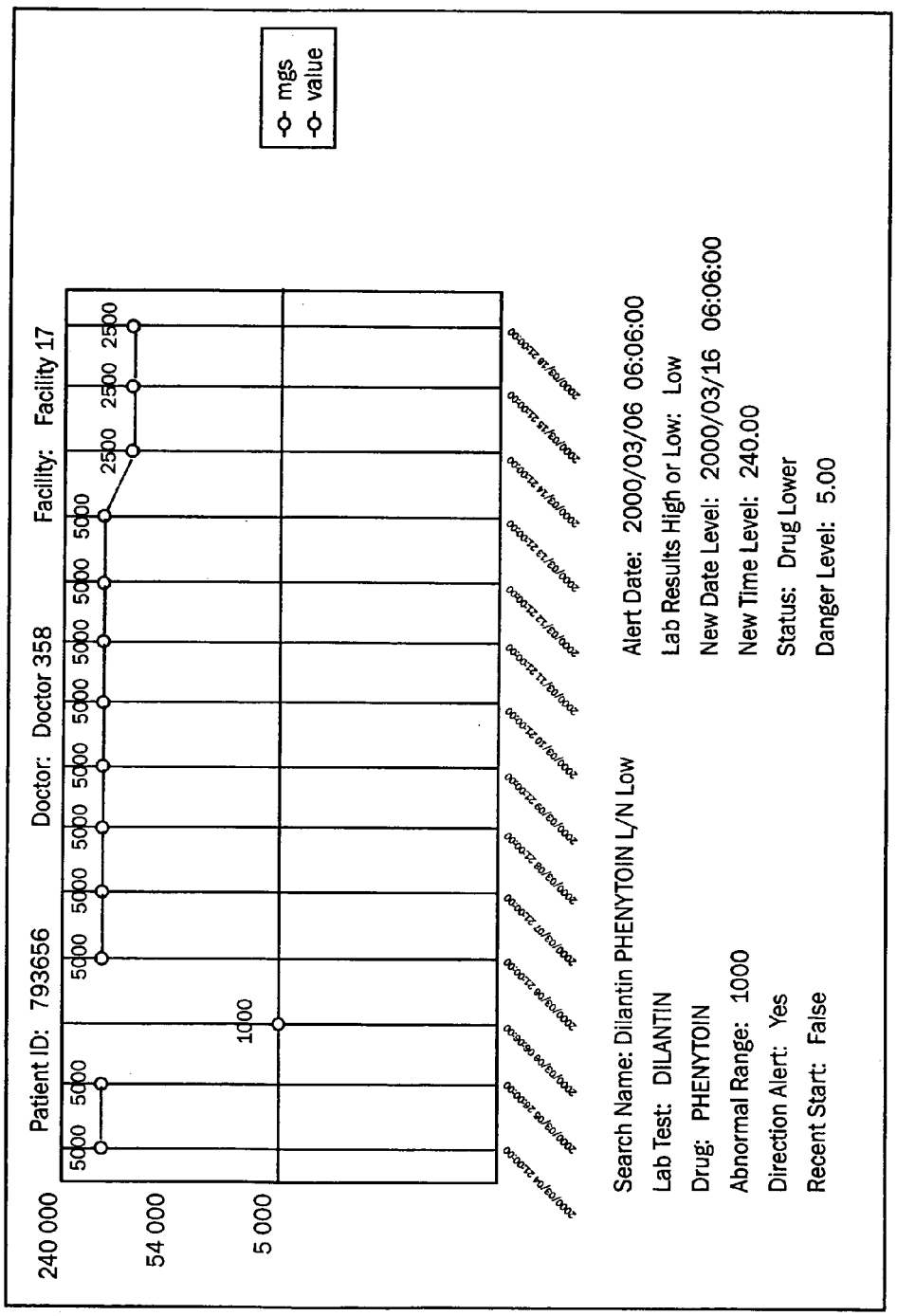
FIG. 15a is an embodiment of a patient graph.
Figure 17A:
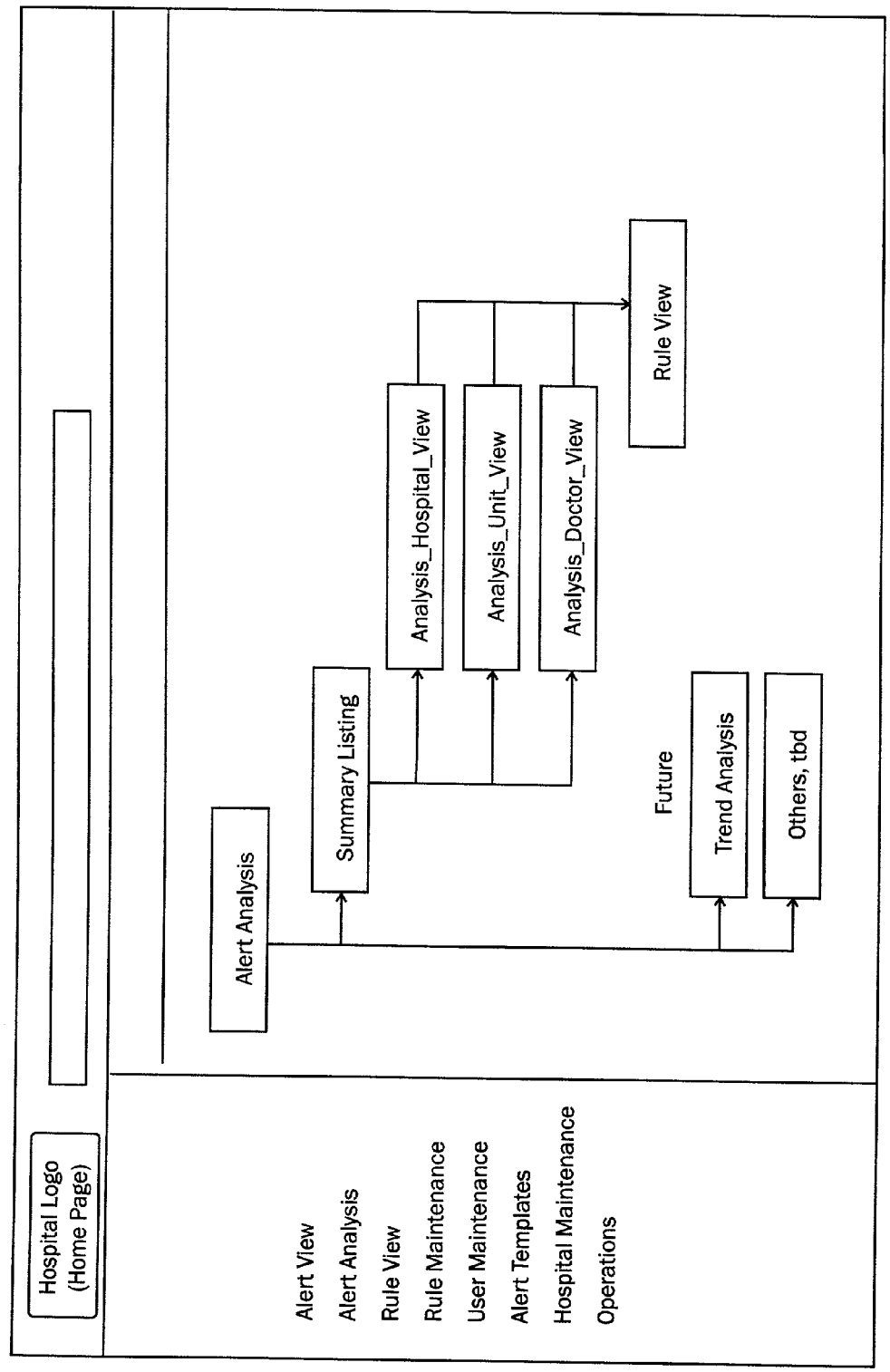
FIG. 17 is an embodiment of a main summary screen.

In one embodiment, an individual patient report is generated utilizing an interactive query. The ADE monitoring system gives the user an option to filter and graph a particular patient's information by defining an ADE rule name, a target lab test, a target drug, an abnormal range, a lab result high or low parameter, a danger level, recent start (instructing the database to consider only recent data), new date look (a feature which enables the computer to estimate what date an action would occur), and new date time (a feature which enables the computer to estimate what time an action would occur). As shown in FIG. 15a, an individual patient report can generate a graphical interpretation of the patients data, or as shown in FIG. 15b the information can be arranged in a tabular format In another embodiment, ADE monitoring system includes a report generation application which can generate predefined reports such as a system report which compiles predefined data for an entire system, an ADE facility report which shows information for a specific facility, a drug management report which breaks out data according to drugs used, ADE reports which performs statistical analysis of ADE's, and an ADE doctor report which shows information for a specific doctor. These reports are predefined and can be generated by simply selecting the function from a menu. As shown in FIG. 15b, these reports can include a specific ADE rule name, a total number of occurrences, a total number of alerts, and a percentage of alerts respective of a total number of occurrences. Alerts such as those shown in FIG. 16 can also be accessed and reviewed individually.

G. User Operation

A user will typically access the ADE monitoring system 10 online by logging onto a web site on a secured intranet. Every authorized user will typically be assigned a unique log on ID and password to enable access. Each user is also typically assigned a security role which limits their ability to access certain information in the ADE monitoring system.

Figure 18:
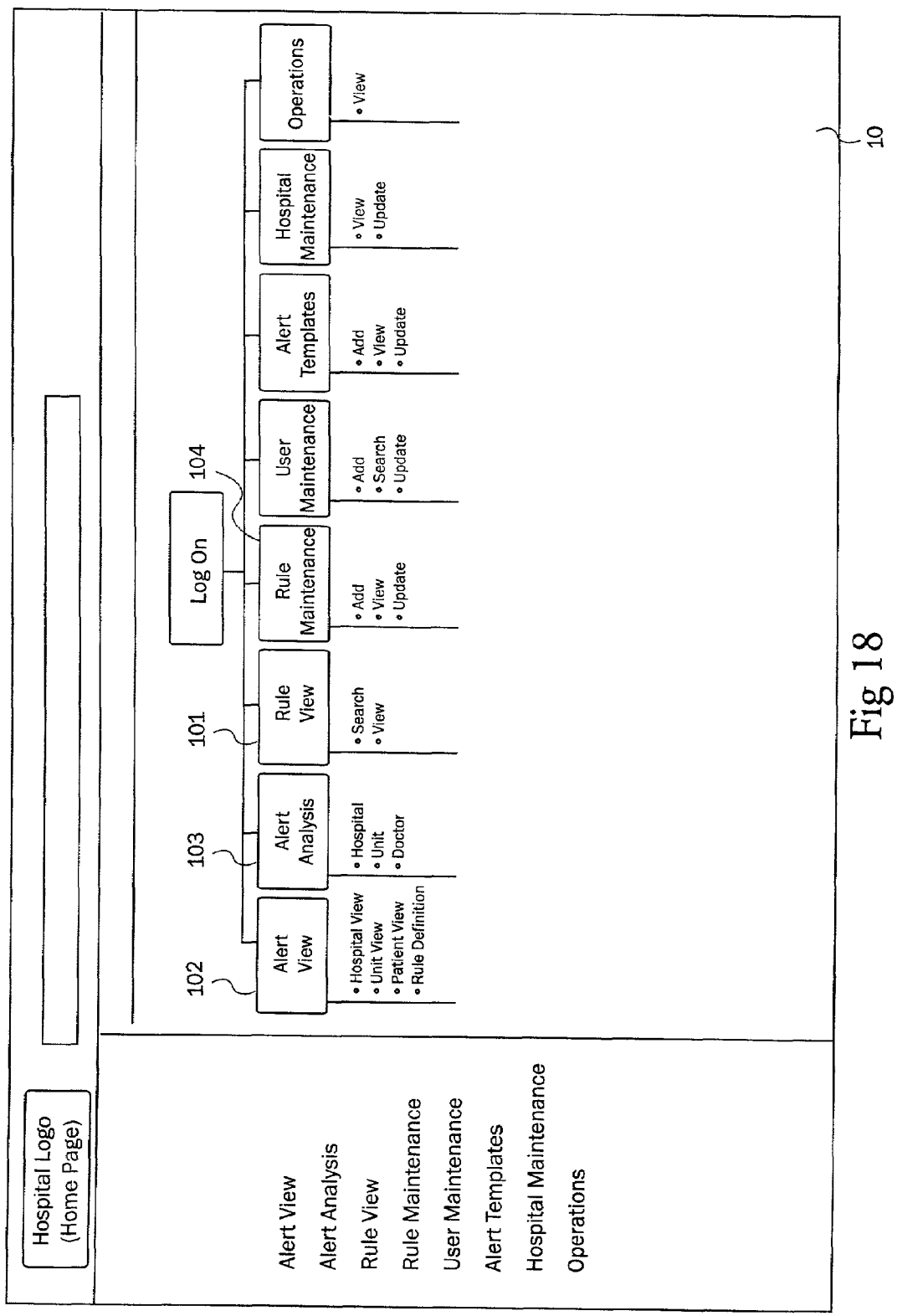
FIG. 18 is an embodiment of a main screen.

As shown in FIG. 18, once logged on, the user is greeted by a primary interface screen 100 which contains selections for navigating to the primary functions of the ADE monitoring system 10. The primary screen includes menu options which enable a user to run a search 101, consult ADE results 102, and 103 and to create and modify ADE rules 104.

Figure 19B:
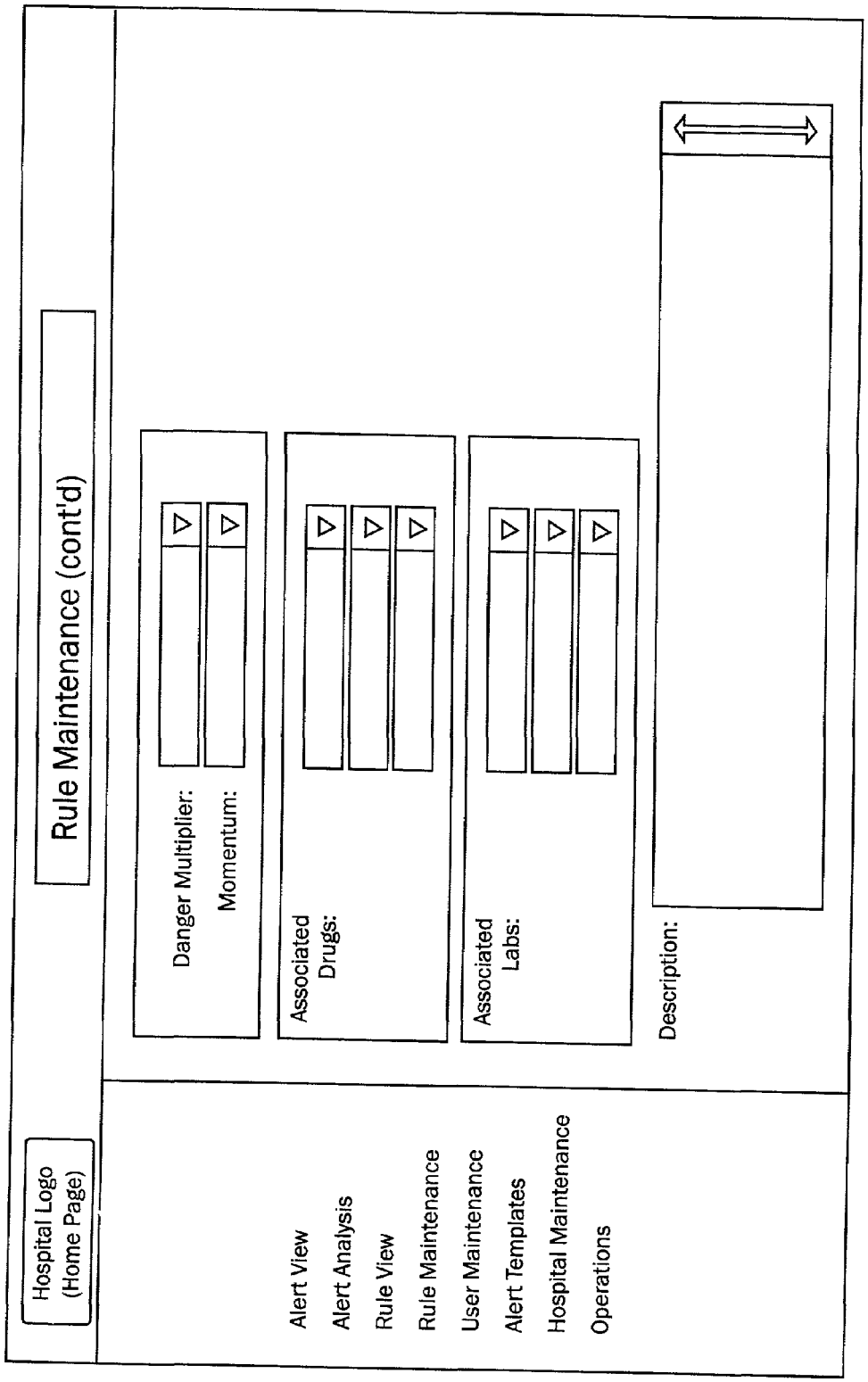

FIGS. 19a and 19b shows a rule maintenance screen 110 to the ADE monitoring system. The screen is used to create new ADE rules, modify existing ADE rules, check the contents of an ADE rule, and to copy the contents of an ADE rule. The screen includes a plurality of data entry fields which enable a user to enter or change values for data fields of an ADE rule.

Figure 20:
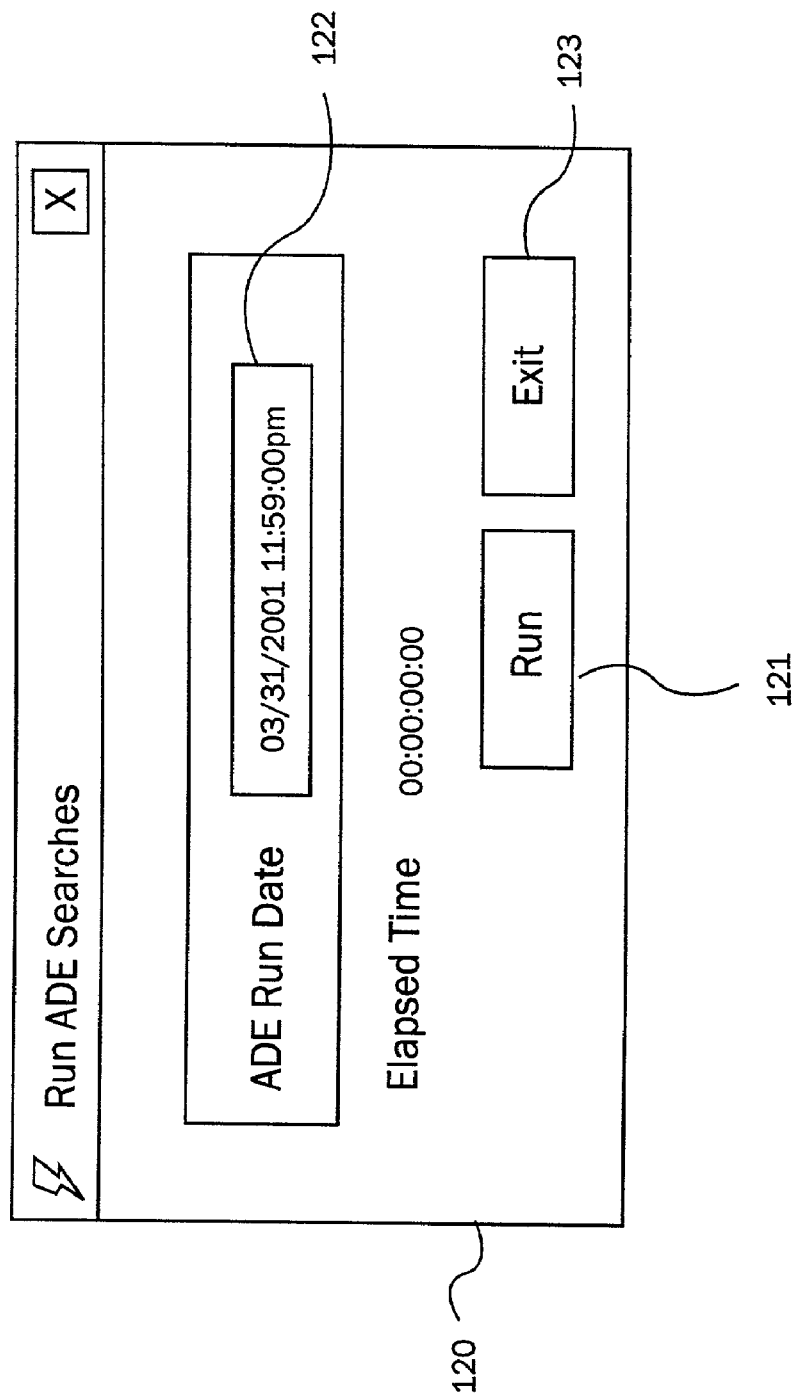
FIG. 20 is an embodiment of a search screen.

FIG. 20 shows a search screen 120 which is used to run an ADE search. A user may instantaneously activate the ADE monitoring process by selecting the Run button 121. A status window 122 defines the exact date and time the ADE monitoring was run. After the ADE monitoring process is completed, the exit button 123 is enabled, and the user can then go back to the primary interface screen 100 by selecting it.

Once back in the primary interface screen 100, the user can view ADE monitoring results by selecting the Alert View 102 and Alert Analysis 103 options. The ADE monitoring results can then be displayed based on a particular individual or a group of individuals by using the patient reports procedures outlined above.

While the present invention has been described with reference to several embodiments thereof, those skilled in the art will recognize various changes that may be made without departing from the spirit and scope of the claimed invention. Accordingly, this invention is not limited to what is shown in the drawings and described in the specification but only as indicated in the appended claims, nor is the claimed invention limited in applicability to one type of computer or computer network. Any numbering or ordering of elements in the following claims is merely for convenience and is not intended to suggest that the ordering of the elements of the claims has any particular significance other than that otherwise expressed by the language of the claim.

What is claimed is:

1. A method of anticipating adverse drug episodes comprising:
    defining a plurality of ADE rules, each having data fields for a lab test name, a value for the lab test, a drug name, and at least one drug/lab linkage parameter relating the lab test name and the drug name; and
    filtering a patient's lab data and pharmacy data using the plurality of definitions.

2. The method of claim 1, and further comprising the additional step of creating a normalized drug table from the patient's pharmacy data, the pharmacy table having data fields for each drug administered, a dosage, and a time administered.

3. The method of claim 2, and further comprising the additional step of creating a normalized lab table from the patient's lab data, the lab table having data fields for a patient id, time of test, name of test, and a test result.

4. The method of claim 3, wherein the step of filtering includes the steps of extracting a lab name, a result of the lab from the lab table and a drug from the drug table and matching it to a lab name, lab result and drug within an ADE rule.

5. The method of claim 1, and further comprising the additional step of importing laboratory data and pharmacy data from a healthcare facility.

6. The method of claim 5, and further comprising the additional step of verifying imported lab data or pharmacy data is formatted in accordance with a predefined format.

7. The method of claim 1, and further comprising the additional steps of computing a cumulative dosage for a drug within a 24 hour period from a date of administration.

8. The method of claim 1, wherein the ADE rules also includes a data field containing a waiting period for a proper corrective action.

9. The method of claim 8, and further comprising the additional steps of filtering subsequent lab data or pharmacy data to determine if a proper corrective action has occurred.

10. The method of claim 9, and further comprising the additional step of alerting a health care provider when a waiting period for a proper corrective action has expired without a proper corrective action occurring.

11. The method of claim 8, and further comprising the additional step of adjusting a waiting period based on a test lab value.

12. The method of claim 8 and further comprising the additional step of adjusting a waiting period based on previous lab test values.

13. The method of claim 1, wherein the lab/data definition includes data fields for associated drugs.

14. The method of claim 13, further comprising the additional step of filtering a patient's previous pharmacy data for an associated drug.

15. The method of claim 1, wherein the lab/data definition includes data fields for an associated test lab and result.

16. The method of claim 15, further comprising the additional step of filtering a patient's lab data for an associated test lab and result.

17. A system for anticipating adverse drug events comprising:
    a central processor having a search engine therein; and
    an ADE rule database in communication with the central processor, a plurality of ADE rules, each having data fields for a lab test name, a value for the lab test, a drug name, and at least one drug/lab linkage parameter being stored in the ADE rule database, the at least one drug/lab linkage parameter relating the lab test name and the drug name.

18. The system of claim 17, wherein the central processor is in communication with a computer network.

19. The system of claim 18, wherein the computer network is an intranet.

20. The system of claim 17, and further comprising a laboratory database and a pharmacy database.

21. The system of claim 17, wherein the central processor includes a web server hosting a web site therein and in communication with an intranet.

22. The system of claim 17, wherein the central processor is in communication with a pharmacy information system and a laboratory information system.

23. The system of claim 17, wherein the central processor is in communication with a nursing station at a medical facility.

24. The system of claim 17, wherein the central processor is in communication with a paging system.

25. The system of claim 17, wherein the central processor includes a web server, an application server, a database server, and a directory server.

26. The system of claim 17 wherein the central processor includes an application for reformatting and integrating pharmacy data and lab data.

27. A method of anticipating adverse drug episodes comprising:
defining a plurality of ADE rules, each having data fields for a lab test name, a value for the lab test, and a drug name, and at least one drug/lab linkage parameter relating the lab test name and the drug name;
storing the plurality of ADE rules within an ADE rules database;
importing a patient's lab data and pharmacy data, the patient's lab data including a lab test name and a lab test result, and the patient's pharmacy data including a name of a drug administered to the patient;
storing the patient's lab test result, lab test name, and a administered drug name within a database;
matching the patient's lab test result, lab test name, and administered drug name with a lab value, lab test name and drug name within an ADE rule.

28. The method of claim 27, and further comprising the additional steps of extracting the lab test name and the lab test result from the patient's lab data and extracting the administered drug name from the patient's pharmacy data.

29. The method of claim 27, wherein the step of storing includes the steps of storing the patient's lab test result and the lab test name within a lab database and storing a name of the drug administered within a pharmacy database.

30. The method of claim 27, and further comprising the additional steps alerting a health care provider when a match occurs.

31. The method of claim 27, and further comprising the additional step of storing a patient's hospital unit, doctor, diagnosis, gender, and age within a database.

32. The method of claim 31, wherein the ADE rule includes a data field for storing a hospital unit, doctor, diagnosis, gender, and age.

33. The method of claim 32, and further comprising the additional steps of matching a patient's hospital unit, doctor, diagnosis, gender, and age with a respective value in an ADE rule.

* * * * *